(12) United States Patent
Miller et al.

(10) Patent No.: US 10,485,548 B2
(45) Date of Patent: Nov. 26, 2019

(54) APPARATUS AND METHOD FOR FORMING A STAPLE LINE WITH TROCAR PASSAGEWAY

(71) Applicant: Ethicon Endo-Surgery, LLC, Guaynabo, PR (US)

(72) Inventors: Christopher C. Miller, Loveland, OH (US); Charles J. Scheib, Loveland, OH (US); Cortney E. Henderson, Loveland, OH (US); Tamara S. Vetro Widenhouse, Clarksville, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 513 days.

(21) Appl. No.: 14/864,310

(22) Filed: Sep. 24, 2015

(65) Prior Publication Data
US 2017/0086848 A1    Mar. 30, 2017

(51) Int. Cl.
*A61B 17/10* (2006.01)
*A61B 17/11* (2006.01)
(Continued)

(52) U.S. Cl.
CPC .... *A61B 17/1155* (2013.01); *A61B 17/06166* (2013.01); *A61B 17/07207* (2013.01);
(Continued)

(58) Field of Classification Search
CPC .......... A61B 17/1155; A61B 17/06166; A61B 17/07207; A61B 17/07292; A61B 17/105;
(Continued)

(56) References Cited

U.S. PATENT DOCUMENTS 4,508,253 A * 4/1985 Green .................. A61B 17/072
227/120
4,805,823 A   2/1989 Rothfuss
(Continued)

FOREIGN PATENT DOCUMENTS

EP   2233080 A1   9/2010
EP   2452634 A1   5/2012
(Continued)

OTHER PUBLICATIONS

International Search report and Written Opinion dated Dec. 6, 2016 for International Application No. PCT/US2016/052105, 15 pages.
(Continued)

*Primary Examiner* — Jing Rui Ou
(74) *Attorney, Agent, or Firm* — Frost Brown Todd LLC

(57) ABSTRACT

An apparatus includes a staple cartridge including a plurality of staples and a deck defining a plurality of openings. Each opening of the plurality of openings is associated with a corresponding staple of the plurality of staples, such that each staple is configured to pass through a corresponding opening of the plurality of openings. The apparatus further includes a deformable feature configured to be coupled to tissue in response to actuation of the staple cartridge. The deformable feature is configured to retain at least one outer portion of stapled tissue in an inwardly directed position relative to an inner portion of stapled tissue.

17 Claims, 30 Drawing Sheets

(51) Int. Cl.
*A61B 17/32* (2006.01)
*A61B 17/072* (2006.01)
*A61B 17/115* (2006.01)
*A61B 17/06* (2006.01)
*A61B 17/00* (2006.01)
*A61B 17/04* (2006.01)

(52) U.S. Cl.
CPC ...... *A61B 17/07292* (2013.01); *A61B 17/105* (2013.01); *A61B 17/1114* (2013.01); *A61B 17/320016* (2013.01); *A61B 2017/00862* (2013.01); *A61B 2017/00867* (2013.01); *A61B 2017/00946* (2013.01); *A61B 2017/0464* (2013.01); *A61B 2017/07221* (2013.01); *A61B 2017/07271* (2013.01); *A61B 2017/07285* (2013.01); *A61B 2017/1103* (2013.01); *A61B 2017/1132* (2013.01); *A61B 2017/1142* (2013.01); *A61B 2017/1157* (2013.01)

(58) Field of Classification Search
CPC ........ A61B 17/1114; A61B 17/320016; A61B 2017/00862; A61B 2017/1132; A61B 2017/00867; A61B 2017/00946; A61B 2017/0464; A61B 2017/07221; A61B 2017/07271; A61B 2017/07285; A61B 2017/1103; A61B 2017/1142; A61B 2017/1157
See application file for complete search history.

(56) References Cited

U.S. PATENT DOCUMENTS

| | | | |
|---|---|---|---|
| 5,014,899 A * | 5/1991 | Presty | A61B 17/07207 227/151 |
| 5,040,715 A * | 8/1991 | Green | A61B 17/07207 227/176.1 |
| 5,205,459 A | 4/1993 | Brinkerhoff et al. | |
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |
| 5,314,435 A * | 5/1994 | Green | A61B 17/115 227/175.1 |
| 5,333,773 A | 8/1994 | Main et al. | |
| 5,350,104 A | 9/1994 | Main et al. | |
| 5,397,324 A * | 3/1995 | Carroll | A61B 17/07207 128/898 |
| 5,415,334 A | 5/1995 | Williamson et al. | |
| 5,441,193 A * | 8/1995 | Gravener | A61B 17/07207 227/175.1 |
| 5,465,895 A | 11/1995 | Knodel et al. | |
| 5,533,661 A | 7/1996 | Main et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 5,833,695 A * | 11/1998 | Yoon | A61B 17/072 227/176.1 |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 7,794,475 B2 | 9/2010 | Hess et al. | |
| 8,211,129 B2 * | 7/2012 | Regadas | A61B 17/1114 606/153 |
| 8,408,439 B2 | 4/2013 | Huang et al. | |
| 8,453,914 B2 | 6/2013 | Laurent et al. | |
| 8,910,847 B2 | 12/2014 | Nalagatla et al. | |
| 9,138,225 B2 | 9/2015 | Huang et al. | |
| 9,161,803 B2 | 10/2015 | Yates et al. | |
| 9,289,207 B2 | 3/2016 | Shelton, IV | |
| 9,463,022 B2 | 10/2016 | Swayze et al. | |
| 9,498,222 B2 | 11/2016 | Scheib et al. | |
| 2002/0151911 A1 * | 10/2002 | Gabbay | A61B 17/072 606/151 |
| 2002/0165559 A1 * | 11/2002 | Grant | A61B 17/07207 606/139 |
| 2003/0183671 A1 * | 10/2003 | Mooradian | A61B 17/115 227/175.1 |
| 2004/0093029 A1 * | 5/2004 | Zubik | A61B 17/072 606/219 |
| 2004/0232201 A1 * | 11/2004 | Wenchell | A61B 17/07207 227/176.1 |
| 2006/0173470 A1 * | 8/2006 | Oray | A61B 17/07207 606/151 |
| 2007/0034669 A1 * | 2/2007 | de la Torre | A61B 17/07207 227/180.1 |
| 2008/0190989 A1 | 8/2008 | Crews et al. | |
| 2009/0120994 A1 * | 5/2009 | Murray | A61B 17/00491 227/180.1 |
| 2010/0065606 A1 * | 3/2010 | Stopek | A61B 17/072 227/176.1 |
| 2011/0087279 A1 | 4/2011 | Shah et al. | |
| 2012/0150206 A1 | 6/2012 | Barikosky et al. | |
| 2012/0234900 A1 * | 9/2012 | Swayze | A61B 17/07207 227/180.1 |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166717 A1 | 6/2014 | Swayze et al. | |
| 2014/0166728 A1 | 6/2014 | Swayze et al. | |
| 2015/0083772 A1 | 3/2015 | Miller et al. | |
| 2015/0083773 A1 | 3/2015 | Miller et al. | |
| 2015/0083774 A1 | 3/2015 | Measamer et al. | |
| 2015/0083775 A1 | 3/2015 | Leimbach et al. | |
| 2016/0374666 A1 | 12/2016 | DiNardo et al. | |
| 2016/0374670 A1 | 12/2016 | Fox et al. | |

FOREIGN PATENT DOCUMENTS

| | | |
|---|---|---|
| EP | 2837337 A1 | 2/2015 |
| EP | 2954857 A1 | 12/2015 |
| WO | WO 2015/138760 A1 | 9/2015 |

OTHER PUBLICATIONS

International Preliminary Report on Patentability dated Mar. 27, 2018 for International Application No. PCT/US2016/052105, 10 pages.
Extended European Search Report dated Dec. 2, 2016 for Application No. 16190452.9, 12 pages.

\* cited by examiner

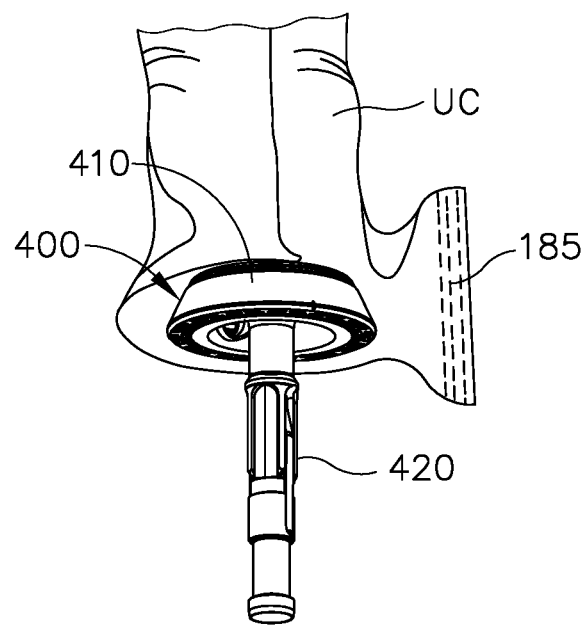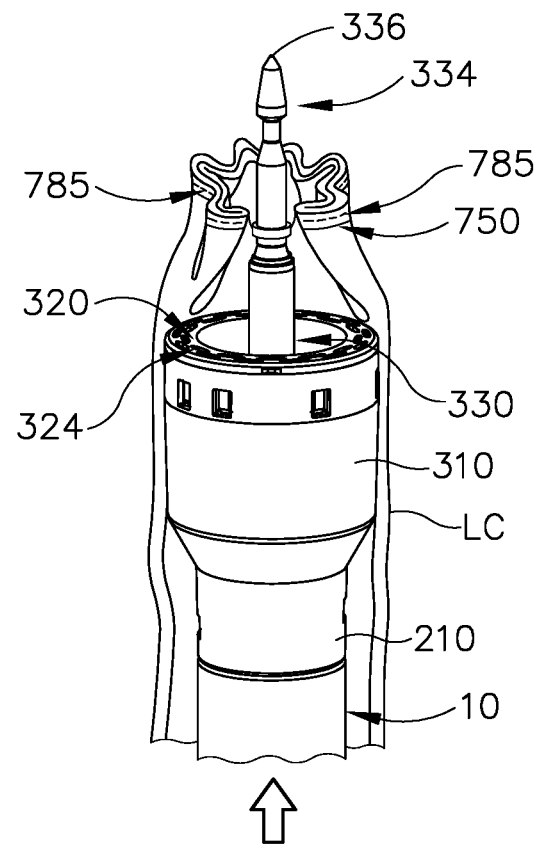
Fig.24

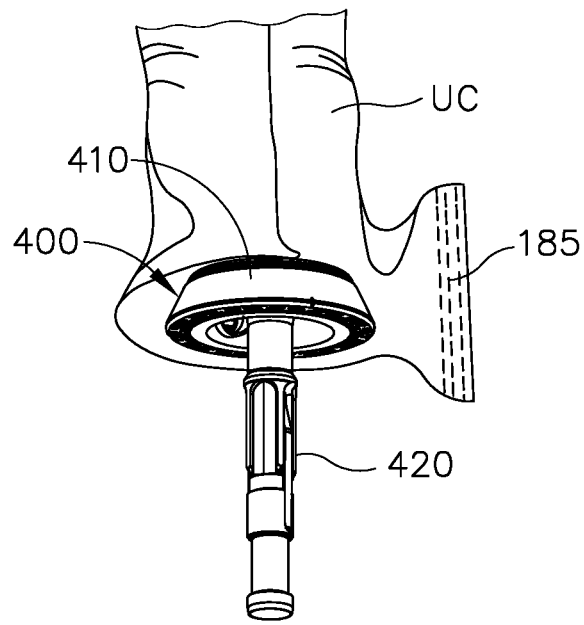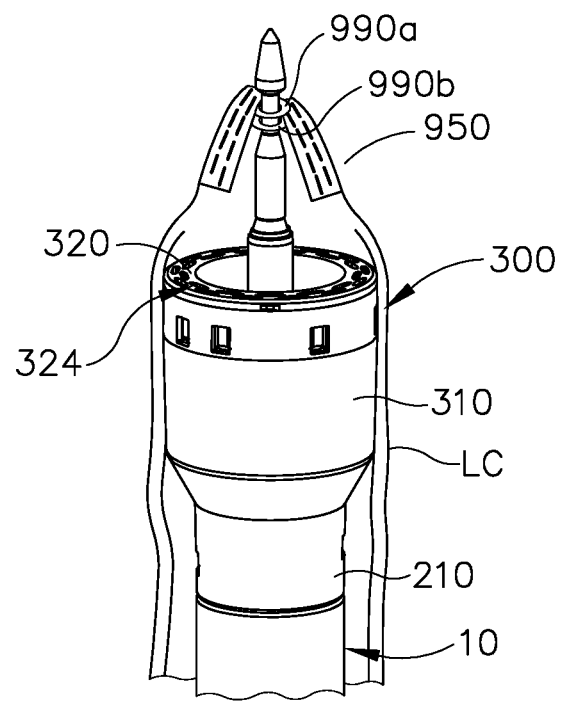
Fig.33

APPARATUS AND METHOD FOR FORMING A STAPLE LINE WITH TROCAR PASSAGEWAY

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015; U.S. Pub. No. 2015/0083773, entitled "Surgical Stapling Instrument with Drive Assembly Having Toggle Features," published Mar. 26, 2015; U.S. Pub. No. 2015/0083774, entitled "Control Features for Motorized Surgical Stapling Instrument," published Mar. 26, 2015; and U.S. Pub. No. 2015/0083775, entitled "Surgical Stapler with Rotary Cam Drive," published Mar. 26, 2015. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 24 depicts a schematic view of severed upper and lower portions of a patient's gastrointestinal tract, with the buttress of FIG. 20 applied to the severed end of the lower portion of the gastrointestinal tract, showing the anvil of FIG. 3 positioned in the upper portion of the gastrointestinal tract and the stapling head assembly of FIG. 4 positioned in the lower portion of the gastrointestinal tract, during a surgical procedure;

FIG. 33 depicts a schematic view of severed upper and lower portions of a patient's gastrointestinal tract, with the buttress of FIG. 30 applied to the severed end of the lower portion of the gastrointestinal tract, showing the anvil of FIG. 3 positioned in the upper portion of the gastrointestinal tract and the stapling head assembly of FIG. 4 positioned in the lower portion of the gastrointestinal tract, during a surgical procedure.

Figure 1:
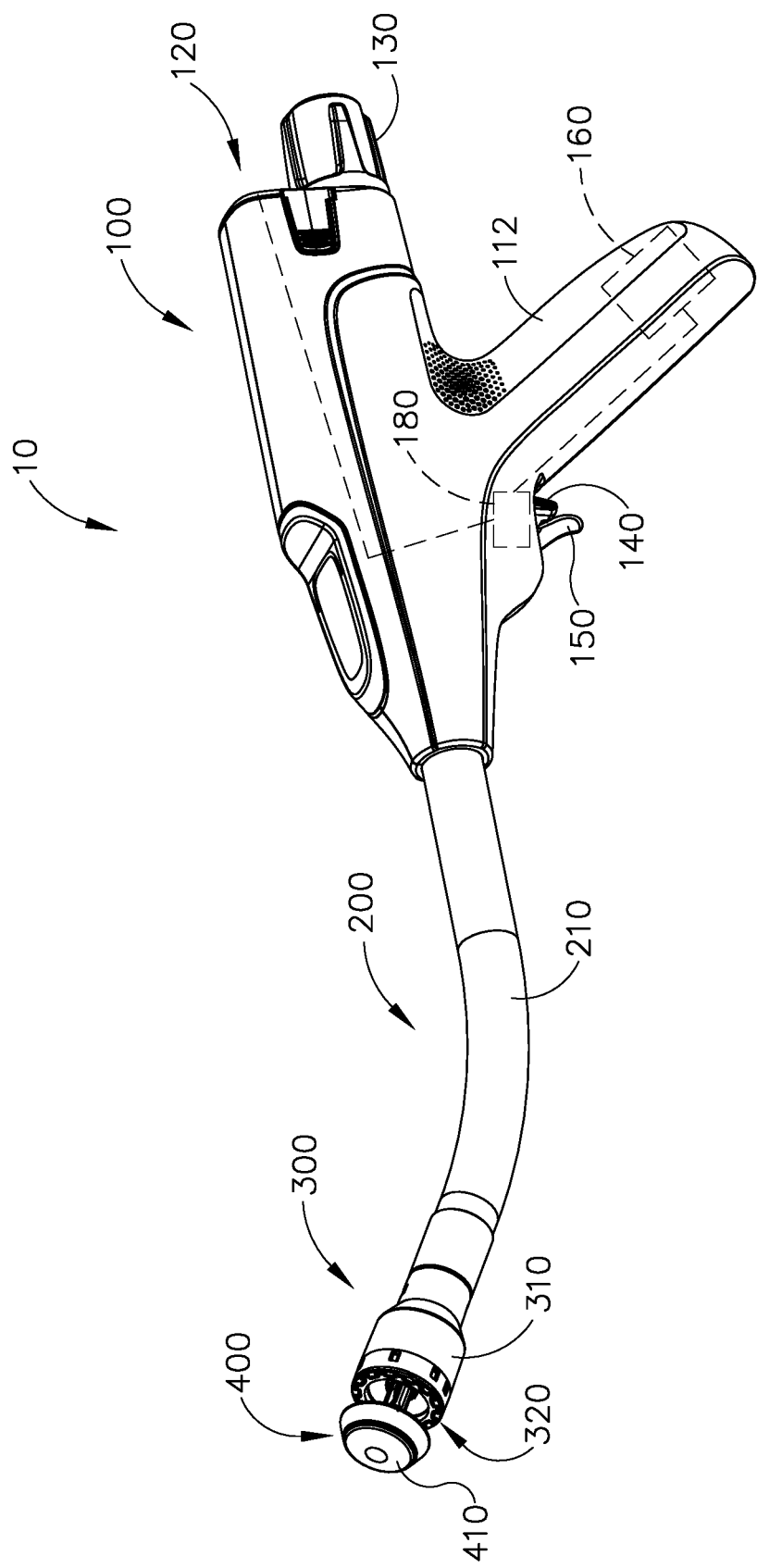
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
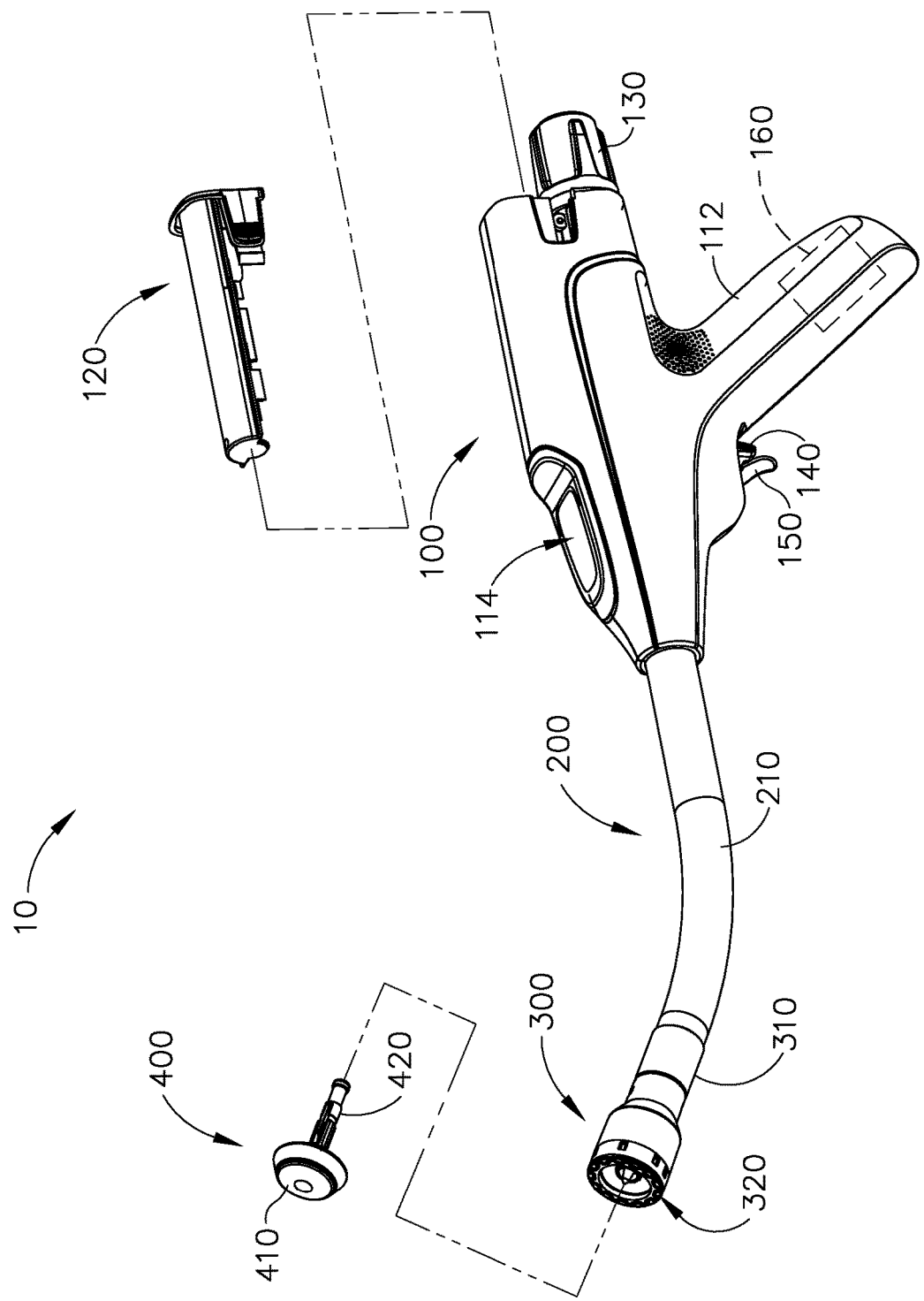
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), an anvil (400), and a removable battery pack (120). Each of these components will be described in greater detail below. It should be understood that, in addition to or in lieu of the following, instrument (10) may be further constructed and operable in accordance with at least some of the teachings of U.S. patent application Ser. No. 14/751,506, entitled "Anvil Stabilization Features for Surgical Stapler," filed Jun. 26, 2015; U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

A. Exemplary Tissue Engagement Features of Circular Stapling Instrument

Figure 3:
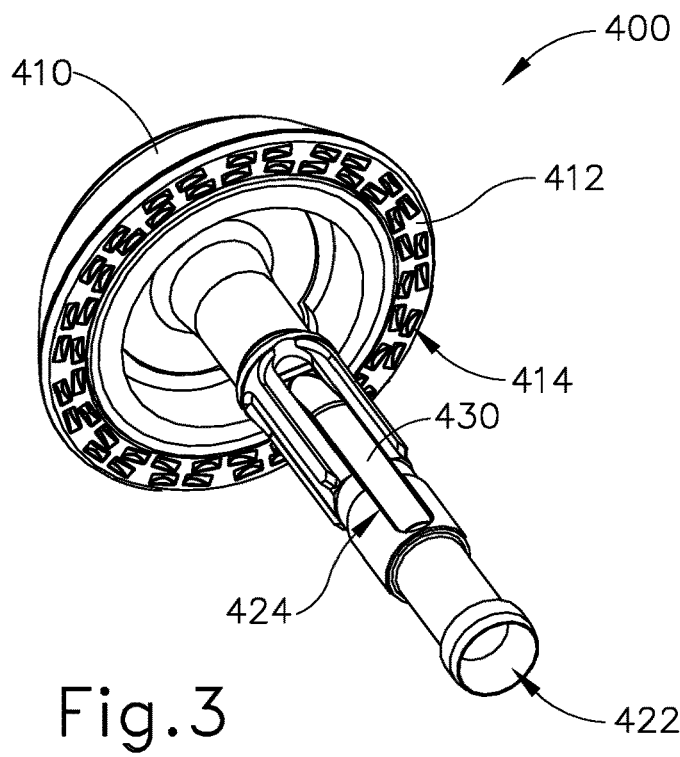
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Stapling head assembly (300) is located at the distal end of shaft assembly (200).

Figure 4:
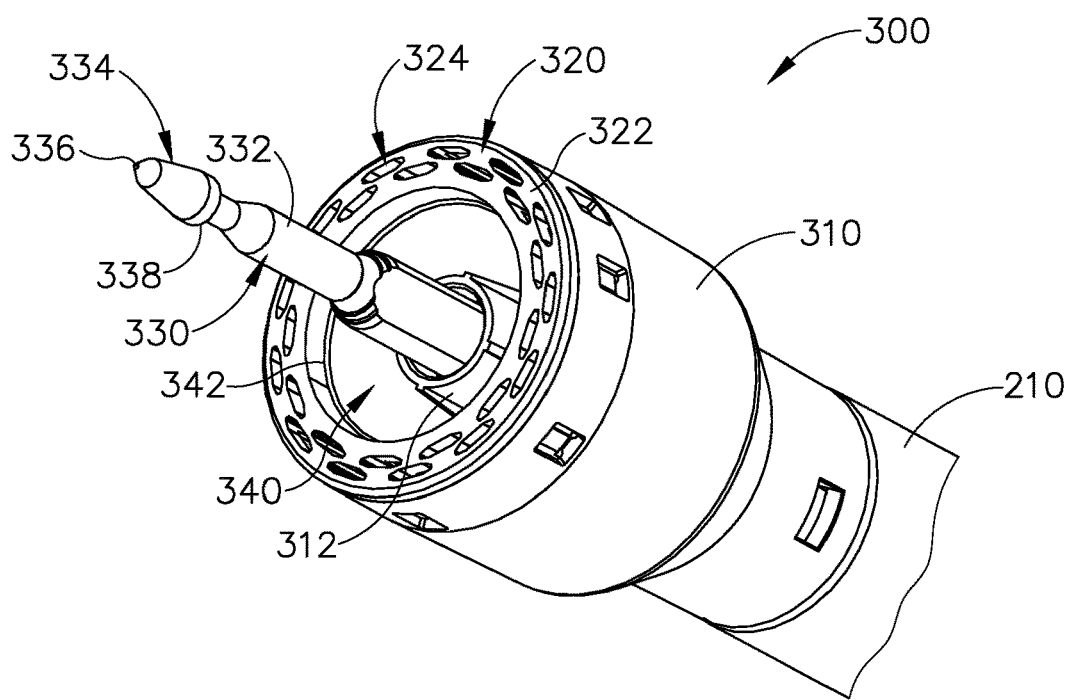
FIG. 4 depicts a perspective view of the stapling head assembly of the circular stapler of FIG. 1.
Figure 5:
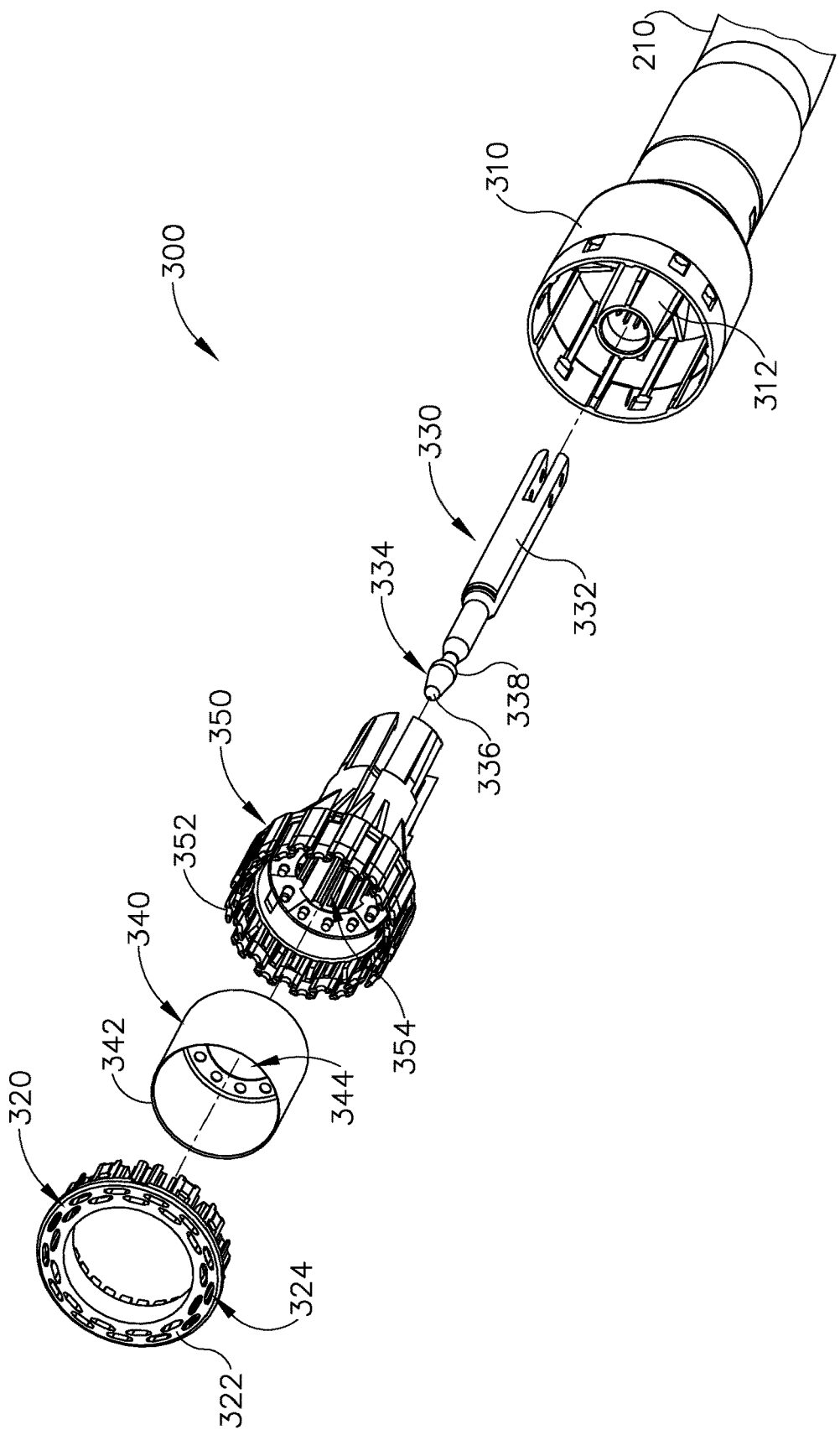
FIG. 5 depicts an exploded perspective view of the stapling head assembly of FIG. 4.

As shown in FIGS. 1-2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4-5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (420). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

Figure 6:
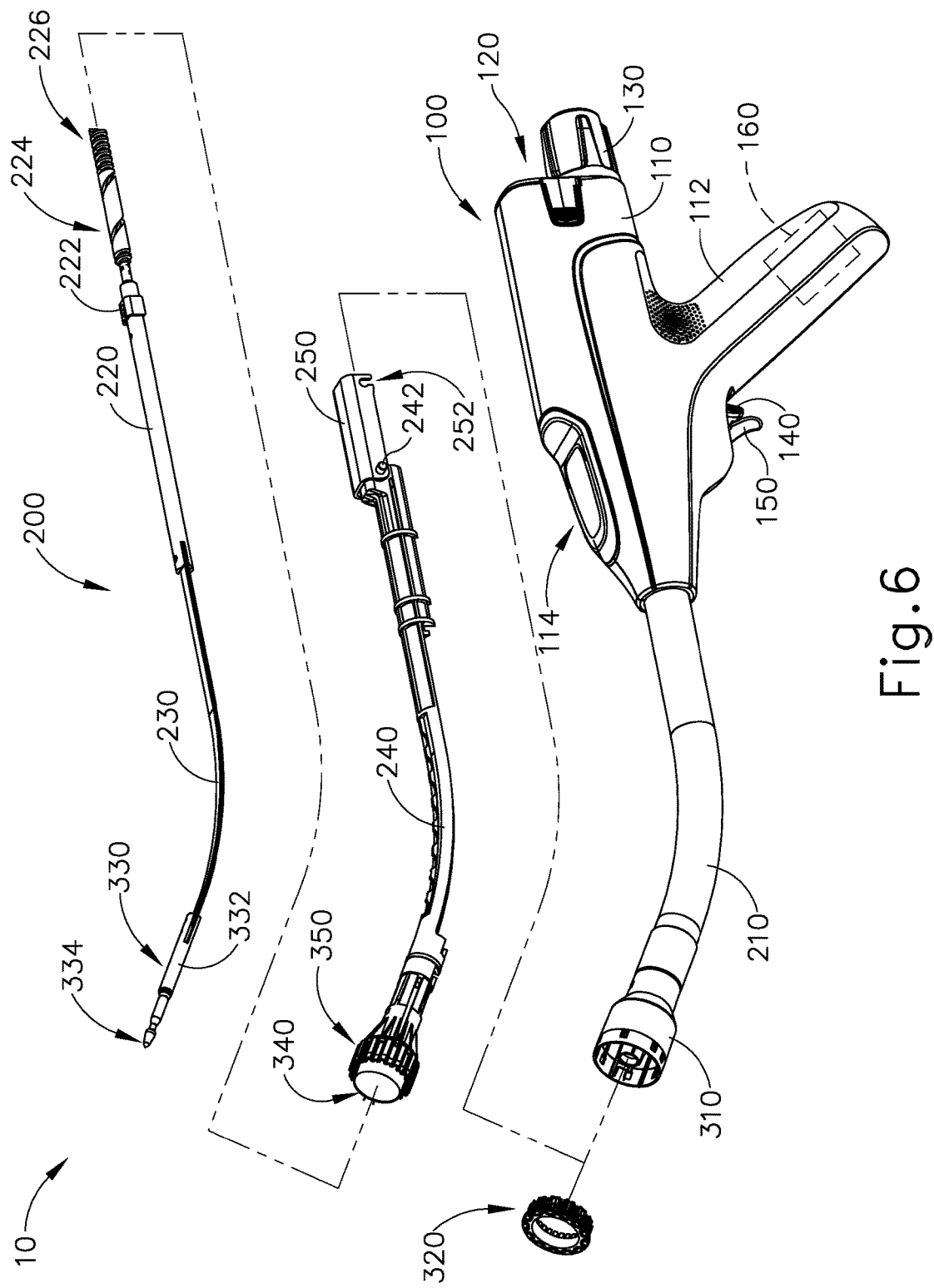
FIG. 6 depicts an exploded perspective view of the circular stapler of FIG. 1, with portions of the shaft assembly shown separately from each other.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section that is configured to facilitate positioning of stapling head assembly (300) within a patient's colon.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance between opposing surfaces (412, 322) of anvil (400) and stapling head assembly (300) until a suitable gap distance has been achieved.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle, such as the paddle shown and described in U.S. patent application Ser. No. 14/751,231, entitled "Surgical Stapler with Reversible Motor," filed Jun. 26, 2015, the disclosure of which is incorporated by reference herein. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery back (120) cannot be removed from handle assembly (100).

C. Exemplary Anastomosis Procedure with Circular Stapling Instrument

FIGS. 7-10 show an exemplary surgical procedure for providing a surgical anastomosis using instrument (10). In various instances, an anastomosis may be performed to remove a section of a patient's gastrointestinal (GI) tract. In the present example, multiple portions of a patient's colon are severed and stapled to resect a diseased portion (C') of the colon (C). The remaining severed and stapled portions of colon (C) are then anastomosed together, as discussed in further detail below.

Figure 7:
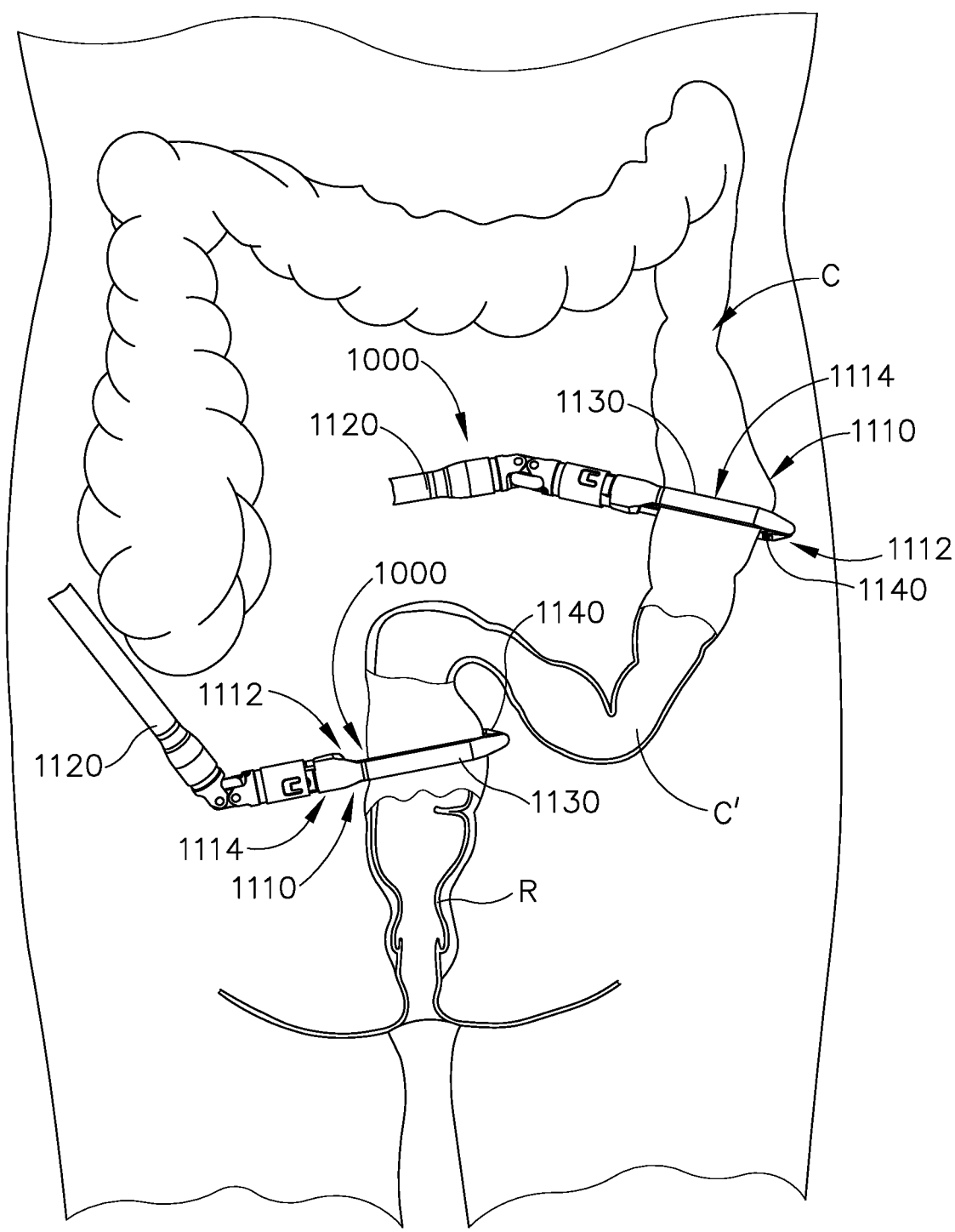
FIG. 7 depicts a schematic view of a lower portion of a patient's gastrointestinal tract, with an endocutter stapler being utilized to staple and sever the gastrointestinal tract at a first location and the endocutter stapler being utilized to staple and sever the gastrointestinal tract at a second location, thereby dividing the gastrointestinal tract into an upper portion, a transected portion, and a lower portion during a surgical procedure.

As shown in FIG. 7, multiple endocutter staplers (1000) may be inserted into a patient to sever and staple portions of the patient's colon (C). By way of example only, endocutter staplers (1000) may be constructed and operable in accordance with at least some of the teachings of U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

In the example shown, endocutter staplers (1000) are inserted into the body laparoscopically via respective trocars. Endocutter stapler (1000) comprises a shaft (1120) and an end effector (1110) extending from the shaft (1120). End effector (1110) comprises a first jaw (1112) and a second jaw (1114). First jaw (1112) comprises a staple cartridge (1140). Staple cartridge (1140) is insertable into and removable from first jaw (1112), though some variations may provide a staple cartridge that is not removable from (or at least readily replaceable from) first jaw (1112). Second jaw (1114) comprises an anvil (1130) that is configured to deform staples ejected from staple cartridge (1140). Second jaw (1114) is pivotable relative to first jaw (1112), though some variations pay provide first jaw (1112) as being pivotable relative to the second jaw (1114). Endocutter staplers (1000) may be configured ad operable in accordance with at least some of the teachings of U.S. Pub. No. 2013/0168435, entitled "Surgical Stapling Instrument with an Articulatable End Effector," published Jul. 4, 2013, the disclosure of which is incorporated by reference. While end effector (1110) is straight and is thus configured to apply a straight line of staples (185) in the present example, in other examples end effector (1110) may be curved and may thus apply a curved line of staples (185).

Figure 8:
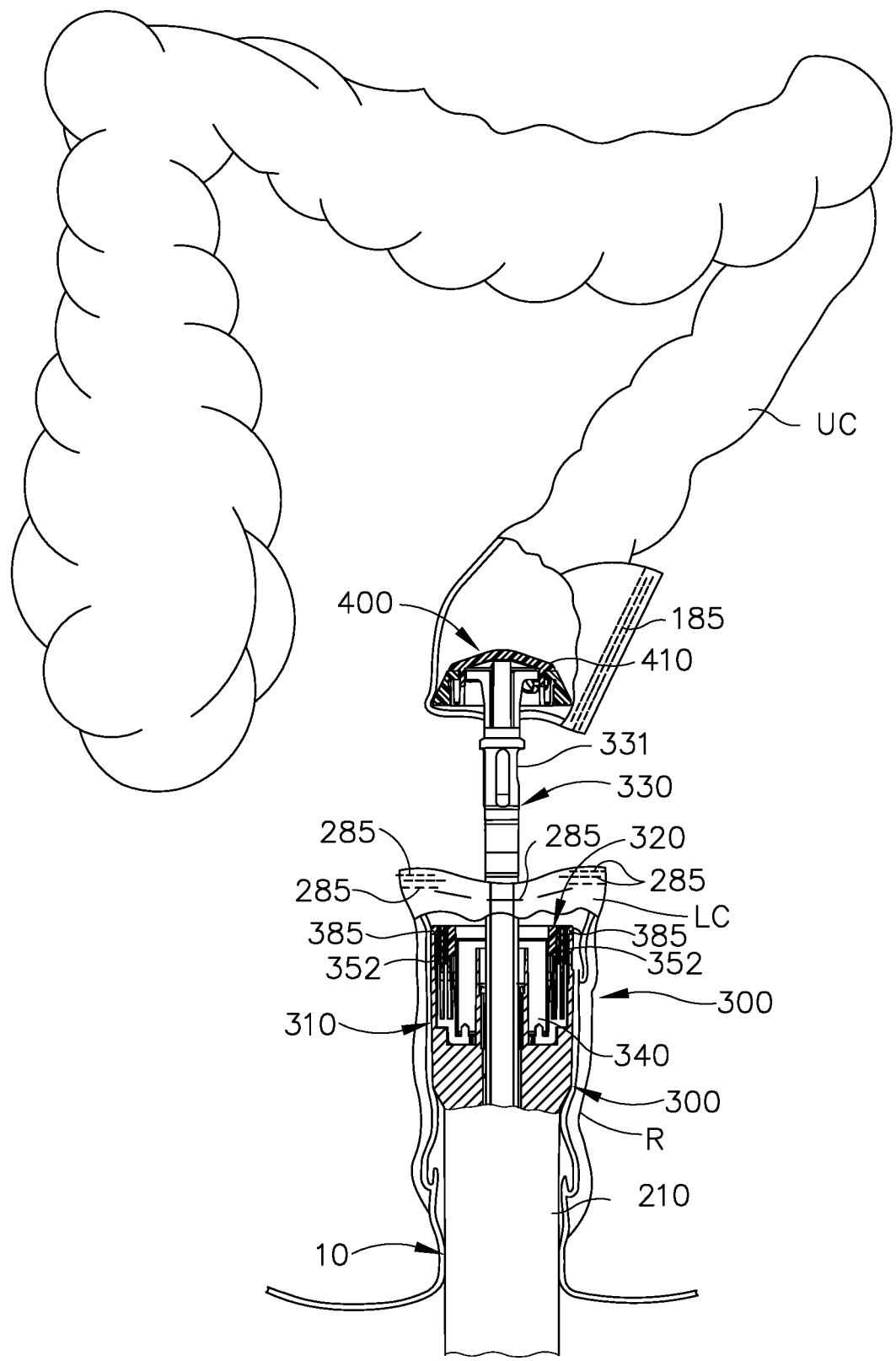
FIG. 8 depicts a schematic view of the gastrointestinal tract of FIG. 7 during another step of the surgical procedure of FIG. 7, showing the anvil of FIG. 3 positioned in the upper portion of the gastrointestinal tract and the stapling head assembly of FIG. 4 positioned in the lower portion of the gastrointestinal tract, with the anvil and the stapling head assembly and adjacent regions of the gastrointestinal tract shown in cross-section.
Figure 9:
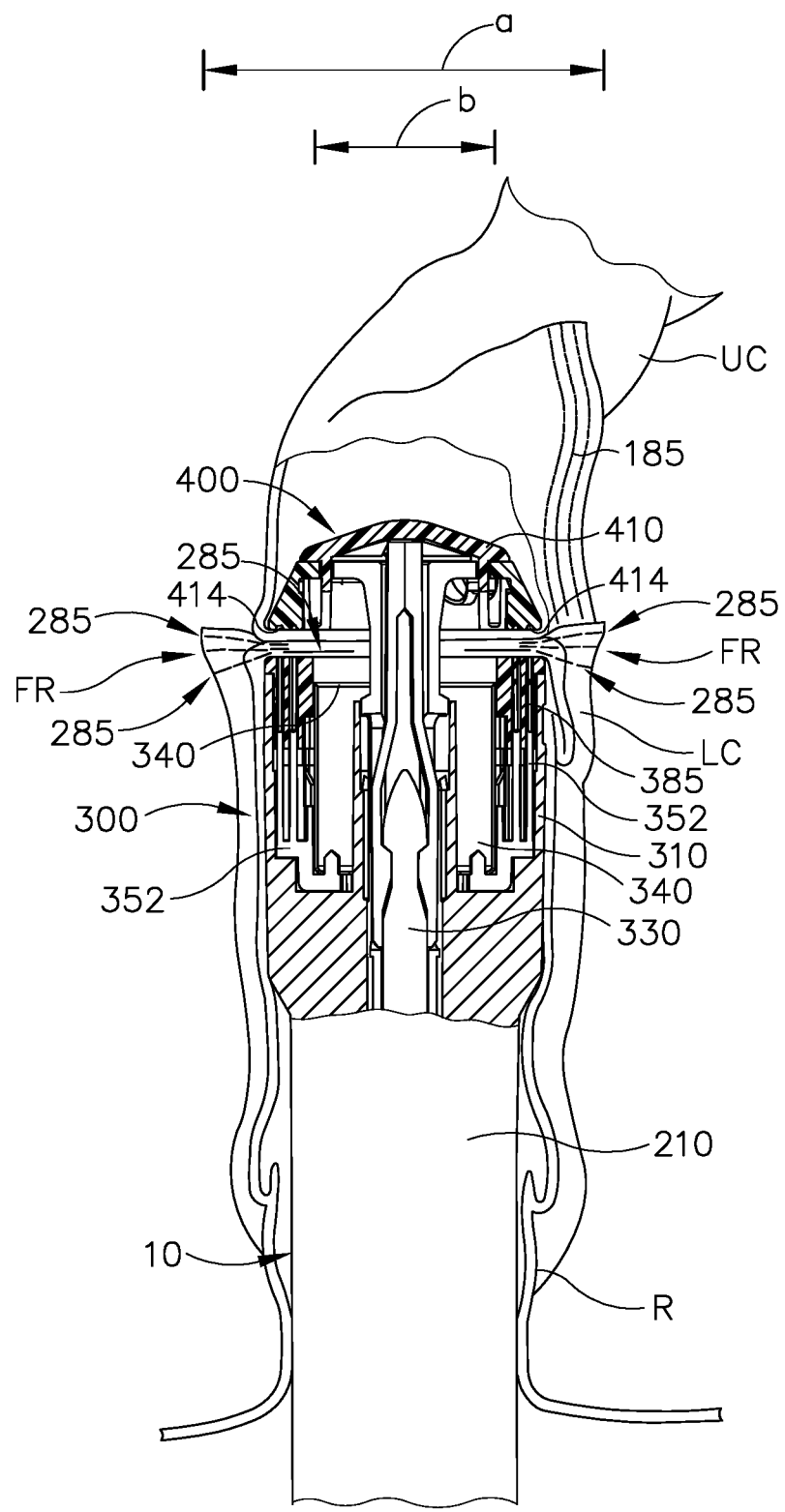
FIG. 9 depicts a schematic view of the gastrointestinal tract of FIG. 7 during another step of the surgical procedure of FIG. 7, showing the upper portion and the lower portion of the patient's gastrointestinal tract being compressed between the anvil and the stapling head assembly of the circular stapler of FIG. 1, with the anvil and the stapling head assembly and adjacent regions of the gastrointestinal tract shown in cross-section.
Figure 10:
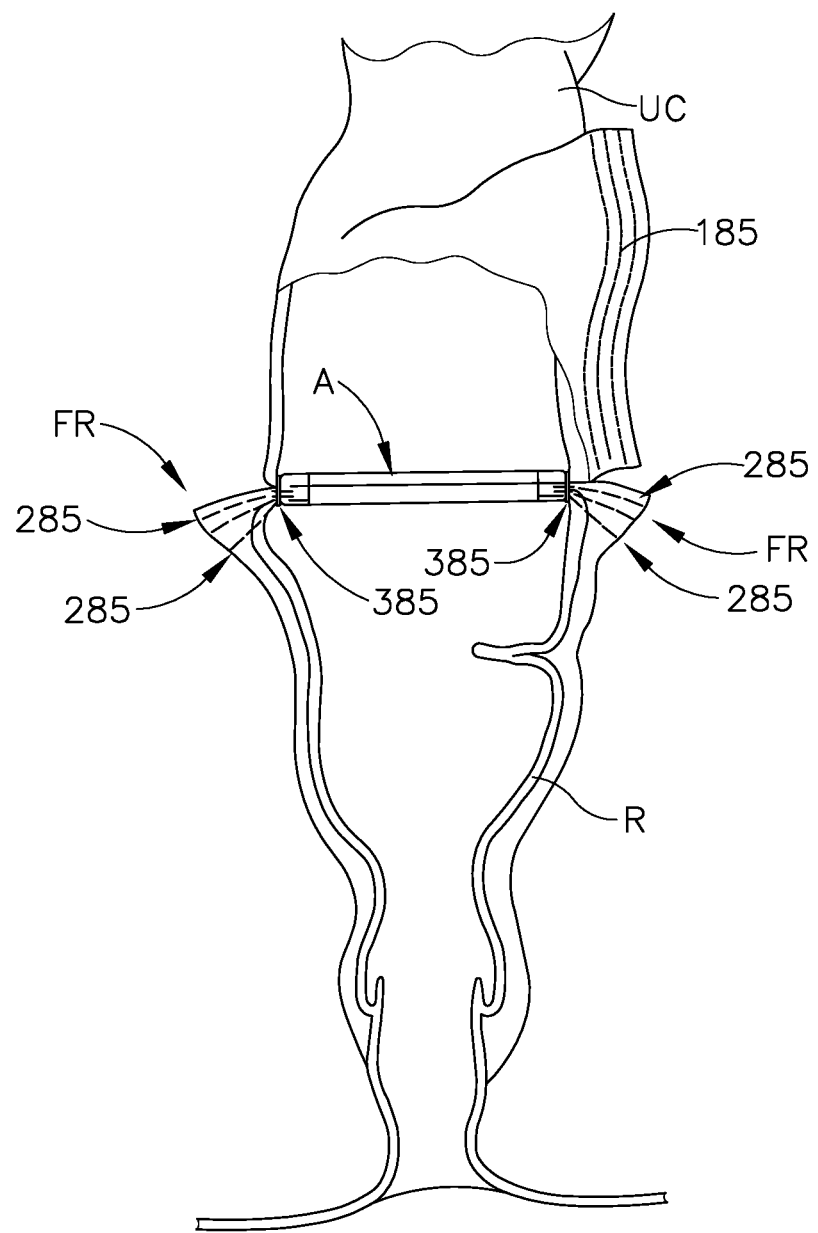
FIG. 10 depicts a schematic view of the gastrointestinal tract of FIG. 7 upon completion of the surgical procedure of FIG. 7, with the upper and lower portions of the patient's gastrointestinal tract joined by staples deployed from the circular stapler of FIG. 1, providing an anastomosis between the upper and lower portions of the patient's gastrointestinal tract, with the anastomosis and adjacent regions of the gastrointestinal tract shown in cross-section.

Anvil (1130) of endocutter stapler (1000) can be opened such that anvil (1130) and staple cartridge (1140) of endocutter stapler (1000) are positioned relative to the patient's colon (C). When anvil (1130) is moved into a closed position, anvil (1130) clamps the colon (C) against staple cartridge (1140). Turning now to FIG. 7, endocutter stapler (1000) can be operated to sever and staple the colon (C) at a first, or upper, location. In the example shown, three linear rows of staples (185) are implanted on the upper side of the severed upper portion (UC) of colon (C) and three rows of the staples (185) are implanted in the adjacent region of the diseased portion (C') of the colon (C). The same endocutter stapler (1000) (if reloaded with another cartridge (1140)), or another endocutter stapler (1000), can be operated to sever and staple the colon (C) at a second, or lower, location. In the present example, three linear rows of staples (285) implanted on the lower side of the severed lower portion (LC) of the colon (C) and three rows of staples (285) are implanted in the adjacent region of the diseased portion (C') of the colon (C). However, in other examples, other suitable configurations of staples may be implanted onto the upper portion (UC) and/or the lower portion (LC) of the colon (C). Once the colon (C) has been transected and stapled at the upper location and the lower location, the diseased portion (C') of the colon can be removed from the patient, as illustrated in FIGS. 8-10.

Referring again to FIGS. 8-9, circular stapler (10) may be utilized to anastomose the upper portion (UC) and the lower portion (LC) of the colon (C). An operator inserts a portion of shaft (210) and stapling head assembly (300) into the rectum (R) of the patient into the lower portion (LC) of the colon (C). In the example shown, a user then inserts trocar (330) through the rows of staples (285). Trocar (330) of circular stapler (10) may then be positioned in the upper portion of the colon C. In various instances, the sidewall of the upper portion of the colon C can be incised and trocar (330) can then be positioned inside the upper portion. Anvil (400) may then be directed into the upper portion of the colon (C) and connected to trocar (330) in the manner discussed above and as shown in FIG. 8.

The operator may then draw anvil (400) toward stapling head assembly (300), in the manner described above (e.g., utilizing knob (130), thus also drawing the upper colon portion (UC) toward the lower colon portion (LC). The operator may then retract trocar (330) until the tissue of the upper colon portion (UC) and the lower colon portion (LC) are compressed against deck (320) as shown in FIG. 9. It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance between opposing surfaces of anvil (400) and stapling head assembly (300) until a suitable gap distance has been achieved, such as in the manner discussed in U.S. patent application Ser. No. 14/751,506, the disclosure of which is incorporated by reference herein. As shown in FIG. 9, flap regions (FR) are formed in the lower portion (LC) of the colon (C) as anvil (400) is drawn toward stapling head assembly (300). These flap regions (FR) extend outwardly from the region of tissue compressed between anvil (400) and stapling head assembly (300).

As discussed above, stapling head assembly (300) is configured to apply annular arrays of staples (385) in the tissue captured between anvil (400) and stapling head assembly (300). Knife member (340) is advanced toward anvil (440) to sever the tissue positioned radially inwardly with respect to the annular arrays of staples (385) applied by circular stapling instrument (10). After the staples (385)

have been fired and tissue has been severed, anvil (400) and stapling head assembly (300) may together be withdrawn from the patient's rectum (R). The incision that was used to insert anvil (400) into the upper portion (UC) of the colon (C) may be closed via suturing or using any other suitable technique.

As shown in FIG. 10, the upper portion (UC) of the colon (C) and the lower portion (LC) of the colon (C) are held together by the annular array of staples (385) deployed by circular stapling instrument (10). The deployed annular array of staples (385) forms an anastomosis (A) that allows fluid tight communication from the upper portion (UC) of the colon (C) to the lower portion (LC) of the colon (C). Some of staples (285) that were deployed by endocutter stapler (1000) will be removed with the tissue that was transected by knife member (340) during actuation of stapling head assembly (300). However, in this example, there are some staples (285) remaining in the outwardly projecting flap regions (FR) in the lower portion (LC) of the colon (C), outside of the anastomosis (A). This is due to the fact that the flap regions (FR) define a width (a) that is substantially greater than the diameter (b) of knife member (340), as best seen in FIG. 9. The flap regions (FR) may nevertheless remain sealed by those remaining staples (285).

II. Exemplary Alternative Staple Cartridges

In some instances, staples (385) that were deployed by circular stapling instrument (10) may overlap with at least some of staples (285) that were deployed by endocutter stapler (1000) in the procedure described above with reference to FIGS. 7-10. Such overlap may prevent proper formation of staples (385), which may compromise the integrity of anastomosis (A) in the long term. In addition or in the alternative, at least some of staples (285) that were deployed by endocutter stapler (1000) may interfere with compression of tissue between anvil (400) and deck member (320) and/or the traversal of knife member (340) through the tissue, which may also compromise the integrity of anastomosis (A) in the long term. Furthermore, there may be instances where the seal provided by staples (285) in flap regions (FR) of the lower portion (LC) of the colon (C) may eventually fail over time. It may therefore be desirable to provide features that prevent the formation of flap regions (FR) and position all of staples (285) within the diameter (b) of knife member (340). Various examples of such features will be described in greater detail below.

Figure 11:
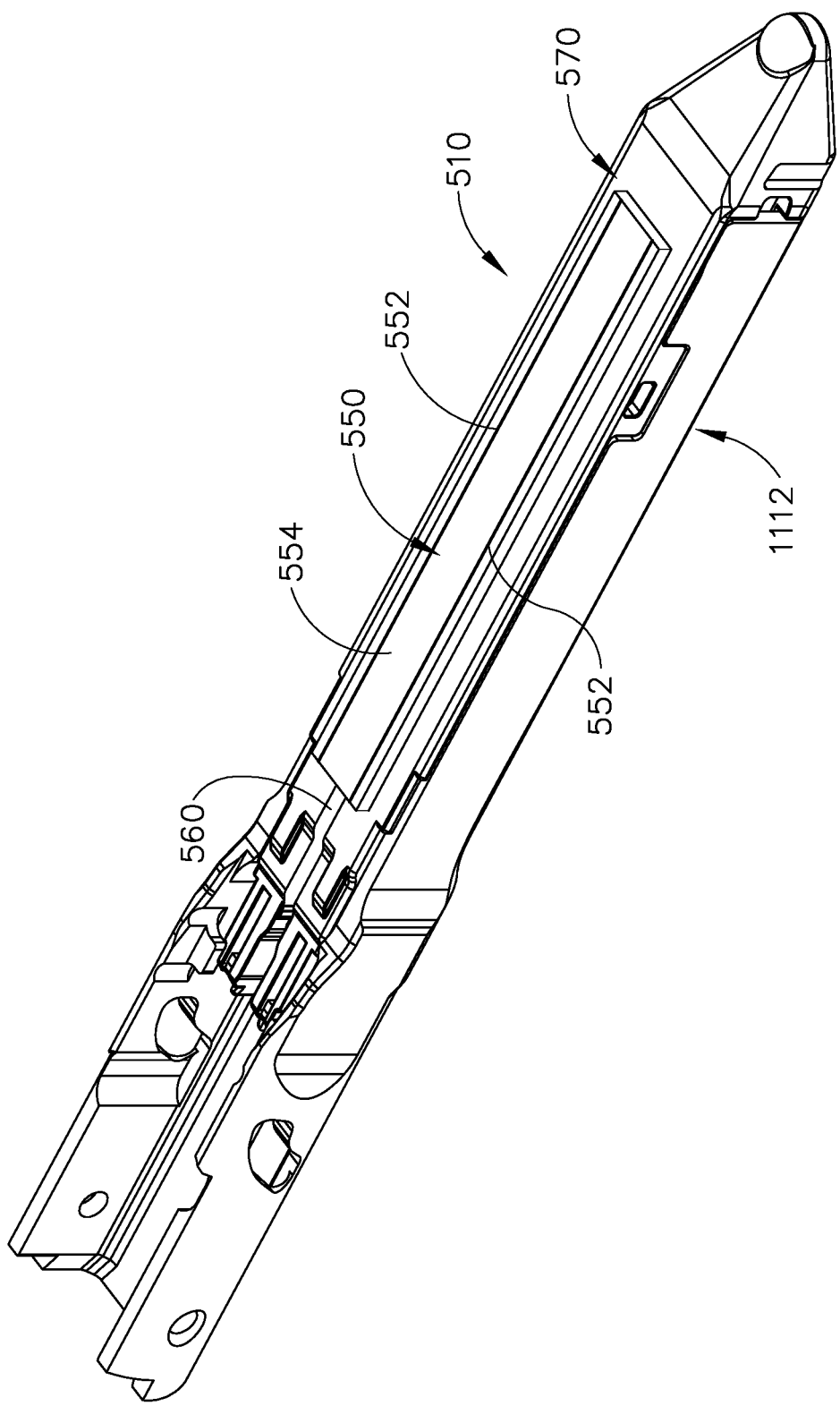
FIG. 11 depicts a perspective view of an exemplary alternative staple cartridge suitable for use in the endocutter stapler of FIG. 7 during performance of the procedure of FIG. 7, including a buttress with malleable elements secured to a deck of the staple cartridge.

A. Exemplary Alternative Staple Cartridge Including Buttress with Malleable Elements FIG. 11 shows an exemplary alternative staple cartridge (510) that may be inserted into first jaw (1112) of end effector (1110) and used during the act of separating the diseased portion (C') of the colon (C) from the lower portion (LC) of the colon (C) as described above with reference to FIG. 7. Staple cartridge (510) is substantially similar to staple cartridge (1140), except for that staple cartridge (510) includes two rows of staple cavities (not shown) on each side of slot (560) of instead of three rows. Therefore, when staple cartridge (510) is incorporated into endocutter stapler (1000), two rows of staples (585) are implanted onto opposing, severed portions of tissue rather than three rows of staples (585).

Staple cartridge (510) of the present example further includes a buttress (550) that is secured to deck (570). Buttress (550) comprises a buttress body (554) with integral malleable elements (552). Various suitable forms that buttress body (554) may take will be apparent to those of ordinary skill in the art in view of the teachings herein. By way of example only, buttress body (554) may be formed by a mesh of woven material that is provided in the form of a thin sheet. Body (554) is configured to be severed in half by a cutting element that traverses slot (560) during actuation of staple cartridge (510). In the example shown, buttress (550) is removably adhered to deck (570), but in other examples buttress (550) may be associated with or coupled to cartridge (510) in a different manner (e.g., via clips, via hook and loop fasteners, etc.). When an end effector (1110) that incorporates staple cartridge (510) is actuated, buttress (550) will be severed along slot (560) and stapled onto tissue along with staples (585), as shown best in FIG. 12.

As shown, malleable elements (552) are coupled to and positioned to rest atop buttress body (554) (e.g., facing anvil). In other examples, however, malleable elements (552) may be otherwise coupled to buttress (550), such as below buttress body (554) (e.g., facing cartridge deck (570)), or may be embedded fully or partially within buttress body (554). Malleable elements (552) are adhered to body (554) in the present example, but in other examples may be coupled to buttress (550) in other manners (e.g., woven through body (554), etc.). In the present example, malleable elements (552) are shown to be straight, linear elements. In other examples, malleable elements (552) may be provided in other configurations, such as curvilinear, zig-zag, etc.

Buttress (550) has only two malleable elements (552) in the present example, such that one of the malleable elements (552) will be implanted with two rows of staples (585) and half of severed body (554) onto one severed portion of tissue and a second one of the malleable elements (552) will be implanted with another two rows of staples (585) and the other half of severed body (554) onto an opposing severed portion of tissue. However, in other examples, there may be more than two malleable (552) elements, such as four, such that a first pair of the malleable elements (552) will be implanted with two rows of staples (585) and half of severed body (554) onto one severed portion of tissue and a second pair of the malleable elements (552) will be implanted with another two rows of staples (585) and the other half of severed body (554) onto an opposing severed portion of tissue. Other suitable configurations of body (554) and malleable elements (552) will be apparent to persons skilled in the art in view of the teachings herein.

In the example shown, each malleable element (552) is formed entirely of a malleable metal. In other examples, however, each malleable element (552) is formed entirely of a non-metallic malleable material. As yet another merely illustrative example, each malleable element (552) may comprise a combination of a malleable material and a non-malleable material. For example, each malleable element (552) may include a malleable core or portion that is coated with a flexible yet non-malleable material. Alternatively, each malleable element (552) may include a non-malleable core or portion that is coated with a malleable material. Various suitable materials and combinations of materials that may be used to form malleable elements (552) will be apparent to those of ordinary skill in the art in view of the teachings herein. In the present example, the entire length of each malleable element (552) is malleable. However, in some examples, only a portion of the length of each malleable element (552) is malleable. For example, outer portions of malleable elements (552) may be malleable while an inner portion therebetween may be non-malleable. Other suitable configurations of malleable elements (552) will be apparent to persons skilled in the art in view of the teachings herein.

Figure 12:
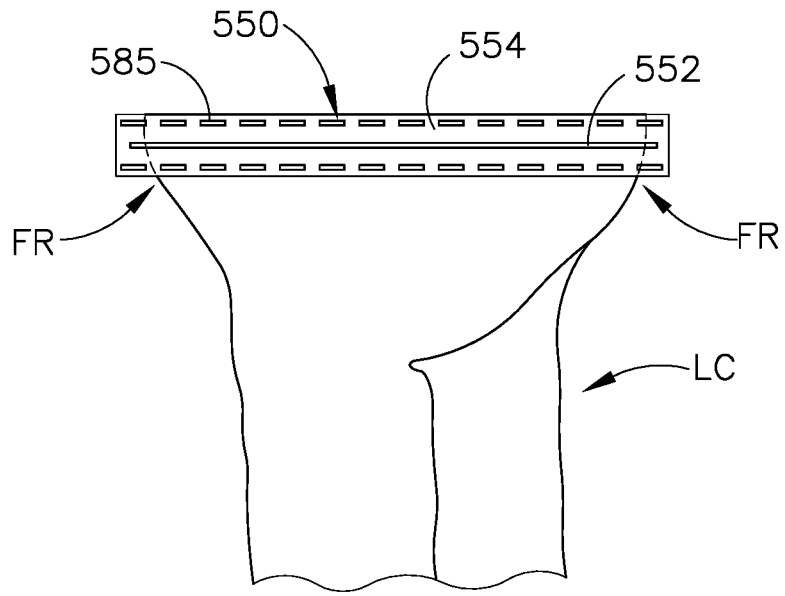
FIG. 12 depicts a side elevational view showing a portion of the gastrointestinal tract after having been stapled and severed utilizing the staple cartridge of FIG. 11, with the buttress and stapled tissue in an unfolded configuration.

As end effector (1100) containing staple cartridge (510) is actuated, drivers of staple cartridge (510) eject staples (585)

out of the corresponding cavities toward anvil (1130), causing buttress (550) to be severed along slot (560) and captured by crowns of the ejected staples (585). Thus, as staples (585) are formed, buttress (550) is captured amongst the formed staples (585) and coupled to the severed and stapled tissue, as shown in FIG. 12. Buttress (550) may then be bent to fold the severed and stapled tissue as shown in FIG. 13 and as described in greater detail below, with malleable elements (552) maintaining the folded configuration.

Figure 14A:
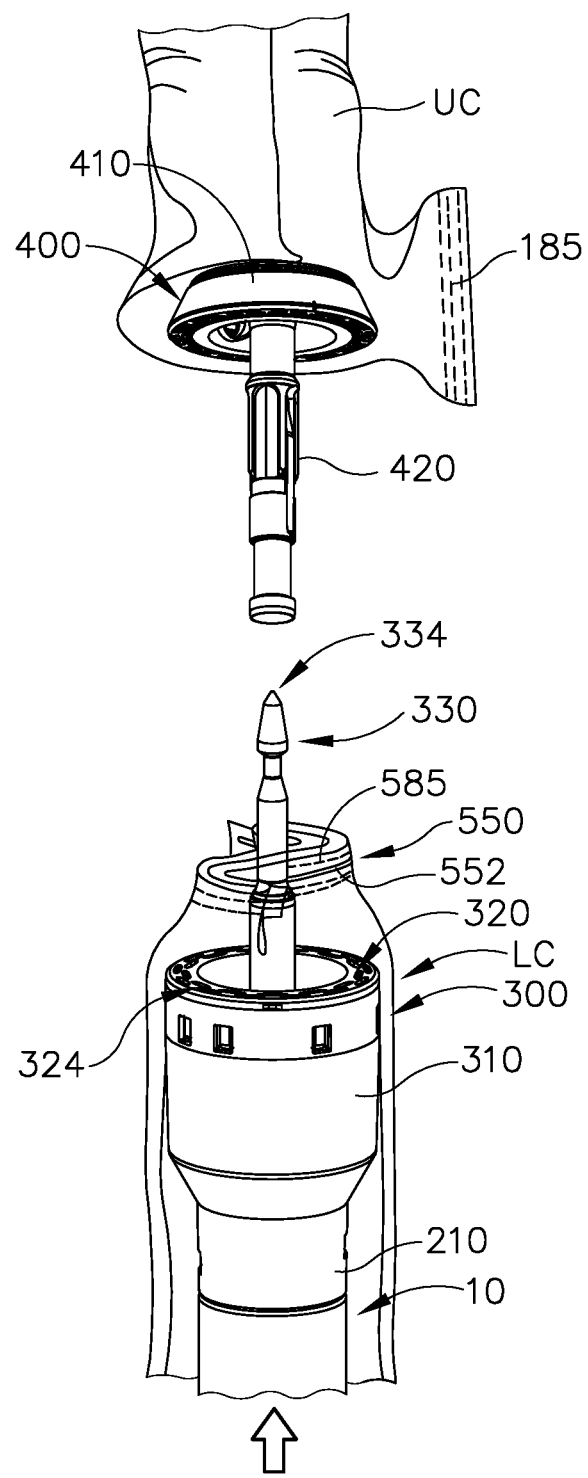
FIG. 14A depicts a schematic view of severed upper and lower portions of a patient's gastrointestinal tract, with the buttress of FIG. 11 applied to the severed end of the lower portion of the gastrointestinal tract, showing the anvil of FIG. 3 positioned in the upper portion of the gastrointestinal tract and the stapling head assembly of FIG. 4 positioned in the lower portion of the gastrointestinal tract, during a surgical procedure.
Figure 14B:
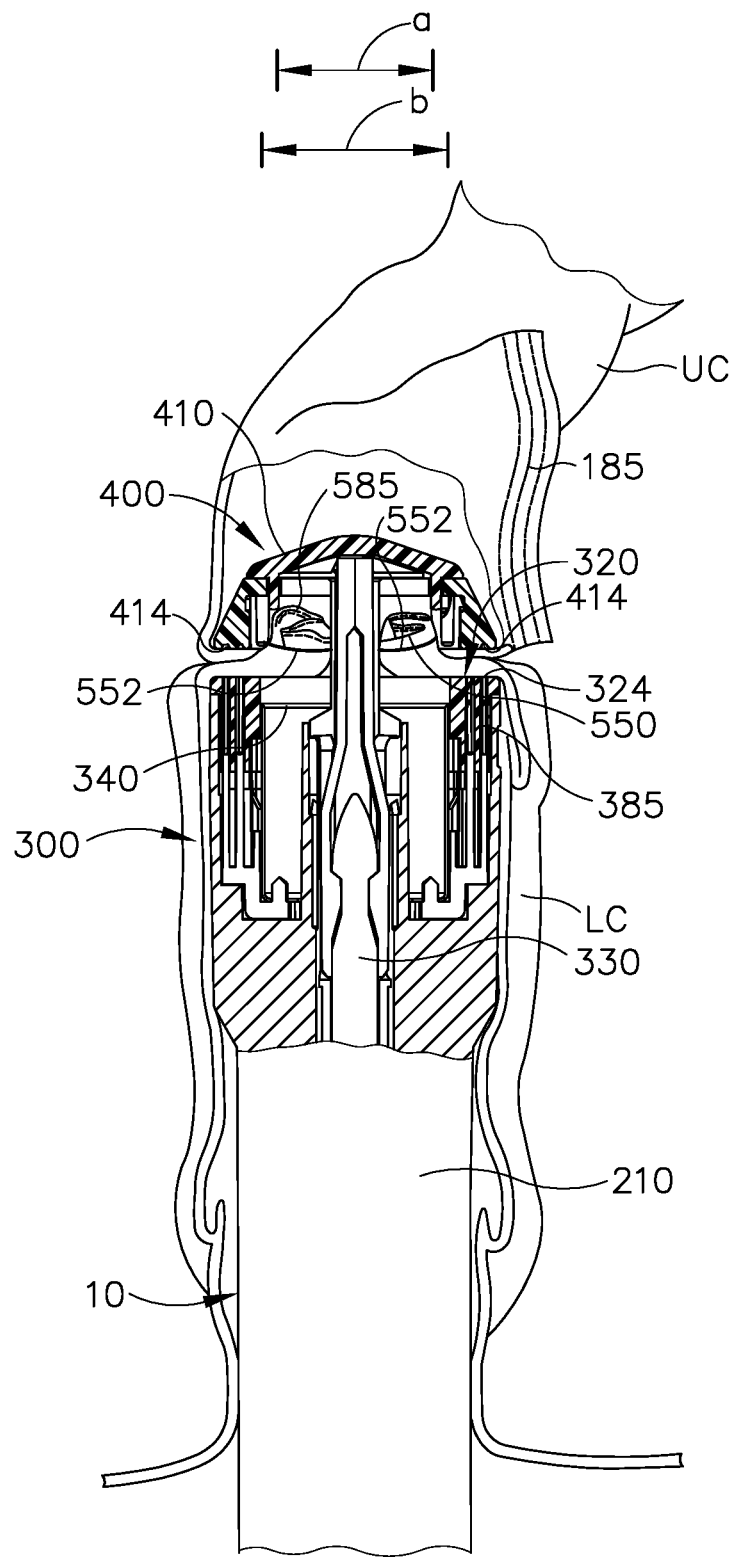
FIG. 14B depicts a schematic view of the gastrointestinal tract of FIG. 14A during another step of the surgical procedure of FIG. 14A, showing the upper portion and the lower portion of the patient's gastrointestinal tract being compressed between the anvil and the stapling head assembly of the circular stapler of FIG. 1, with the anvil and the stapling head assembly and adjacent regions of the gastrointestinal tract shown in cross-section.
Figure 14C:
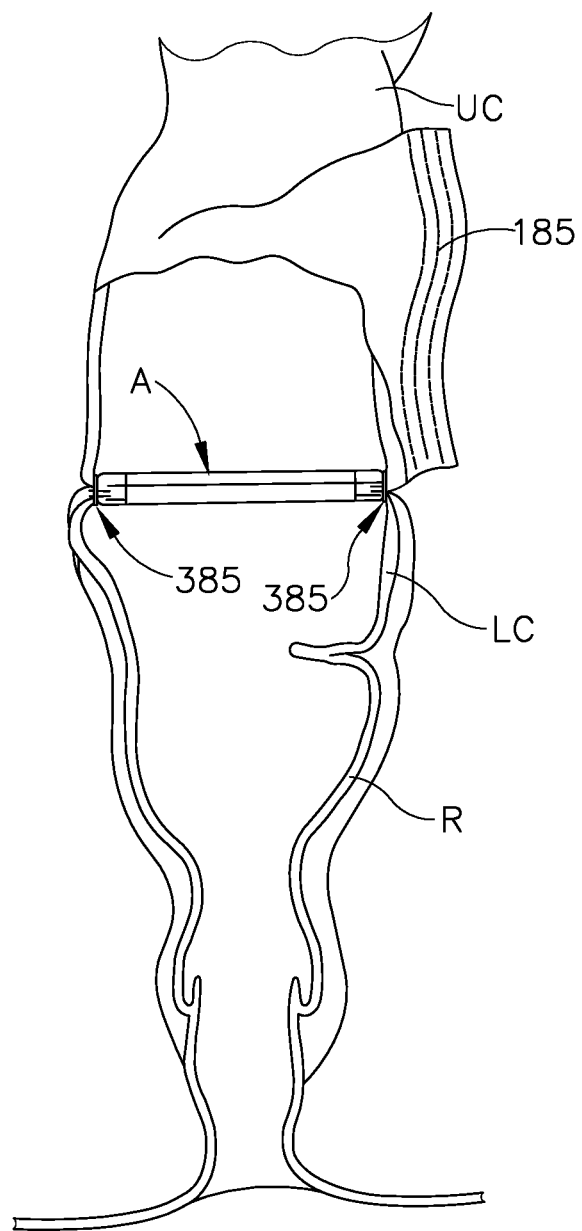
FIG. 14C depicts a schematic view of the gastrointestinal tract of FIG. 14A upon completion of the surgical procedure of FIG. 14A, with the upper and lower portions of the patient's gastrointestinal tract joined by staples deployed from the circular stapler of FIG. 1, providing an anastomosis between the upper and lower portions of the patient's gastrointestinal tract, with the anastomosis and adjacent regions of the gastrointestinal tract shown in cross-section.

FIGS. 14A-14C show steps of an anastomosis procedure similar to the procedure shown in FIGS. 7-10. In FIG. 14A, the upper colon portion (UC) and the lower colon portion (LC) are shown to have been severed and stapled in a similar manner to that shown in FIGS. 7-8. However, in this example the lower colon portion (LC) has been severed and stapled utilizing staple cartridge (510). The lower colon portion (LC) therefore includes staples (585) and buttress (550) coupled thereto in the manner discussed above. As shown, a portion of shaft (210) and stapling head assembly (300) are inserted into the rectum (R) of the patient and into the lower portion (LC) of the colon (C). In the example shown, trocar (330) is inserted through the line of staples (585) such that trocar (330) is exposed out of lower colon portion (LC). Anvil (400) is shown to be positioned in the upper portion (UC) of the colon (C), with shank (420) extending through an opening of the upper colon portion (UC).

Figure 13:
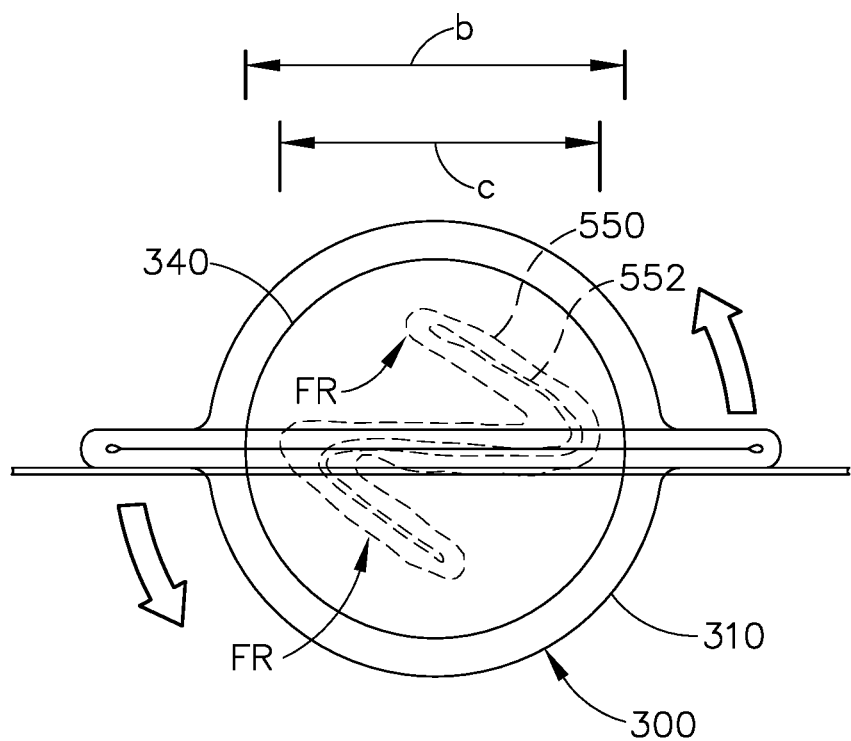
FIG. 13 depicts a top plan view of the portion of the gastrointestinal tract of FIG. 12, with the buttress and stapled tissue in a folded configuration.

As shown in FIG. 14A (and as also shown in FIG. 13), each end of the severed and stapled lower portion (LC) has been folded inwardly to form a "Z" shaped configuration. Therefore, at least part of the lower colon portion (LC) is shown to be drawn radially inwardly toward trocar (330), such that the line of staples (585) lies within the cutting line of knife (340). In other words, the flap regions (FR) are folded inwardly. Various suitable instruments and techniques that may be used to fold the flap regions (FR) of tissue and buttress (510) will be apparent to those of ordinary skill in the art in view of the teachings herein.

As noted above, malleable members (552) hold the severed tissue and buttress body (554) in the folded configuration shown in FIGS. 13-14A. The circular cutting line of knife member (340) is defined by the diameter (b) of knife member (340). As shown in FIGS. 13 and 14B, when the severed tissue and buttress (510) are folded inwardly, the severed tissue at the end of lower colon portion (LC) defines a width (c) that is smaller than the diameter (b) of knife member (340). Thus, all of the applied staples (585), buttress (500), and all of the tissue at the severed end of lower colon portion (LC) are positioned within a cylindrical plane defined by knife member (340).

With malleable members (552) holding the severed tissue and buttress body (554) in the folded configuration to secure flap regions (FR) in an inwardly folded configuration, the operator then connects shank (420) to trocar (330) in the manner discussed above. Alternatively, the operator may fold of flap regions (FR) inwardly after shank (420) and trocar (330) are coupled to one another. Referring to FIG. 14B, the operator may then draw anvil (400) toward stapling head assembly (300), in the manner described above (e.g., utilizing knob (130)), thus also drawing the upper colon portion (UC) toward the lower colon portion (LC). The operator may then retract trocar (330) until the tissue of the upper colon portion (UC) and the lower colon portion (LC) are compressed against the deck member (320) to achieve a desirable gap distance, as shown in FIG. 14B and discussed above.

The operator may then actuate trigger (150) to actuate stapling head assembly (300), resulting in the stapling and severing of tissue in a similar manner as shown in FIG. 9 to form an anastomosis (A). However, due to the position of the applied staples (585) and all of the tissue at the severed end of lower colon portion (LC) being radially inward of the cut line of circular knife (340) as discussed above, all of the tissue in which staples (585) are applied is severed and no staples (585) are disposed in the tissue that remains at the resulting anastomosis (A) site as shown in FIG. 14C. Moreover, staples (585) do not impede the successful operation of circular stapler (10), and there are no flap regions (FR) extending outwardly from the anastomosis (A) site. The severed portion of tissue including staples (585) may be removed by the user via the patient's rectum.

Figure 15:
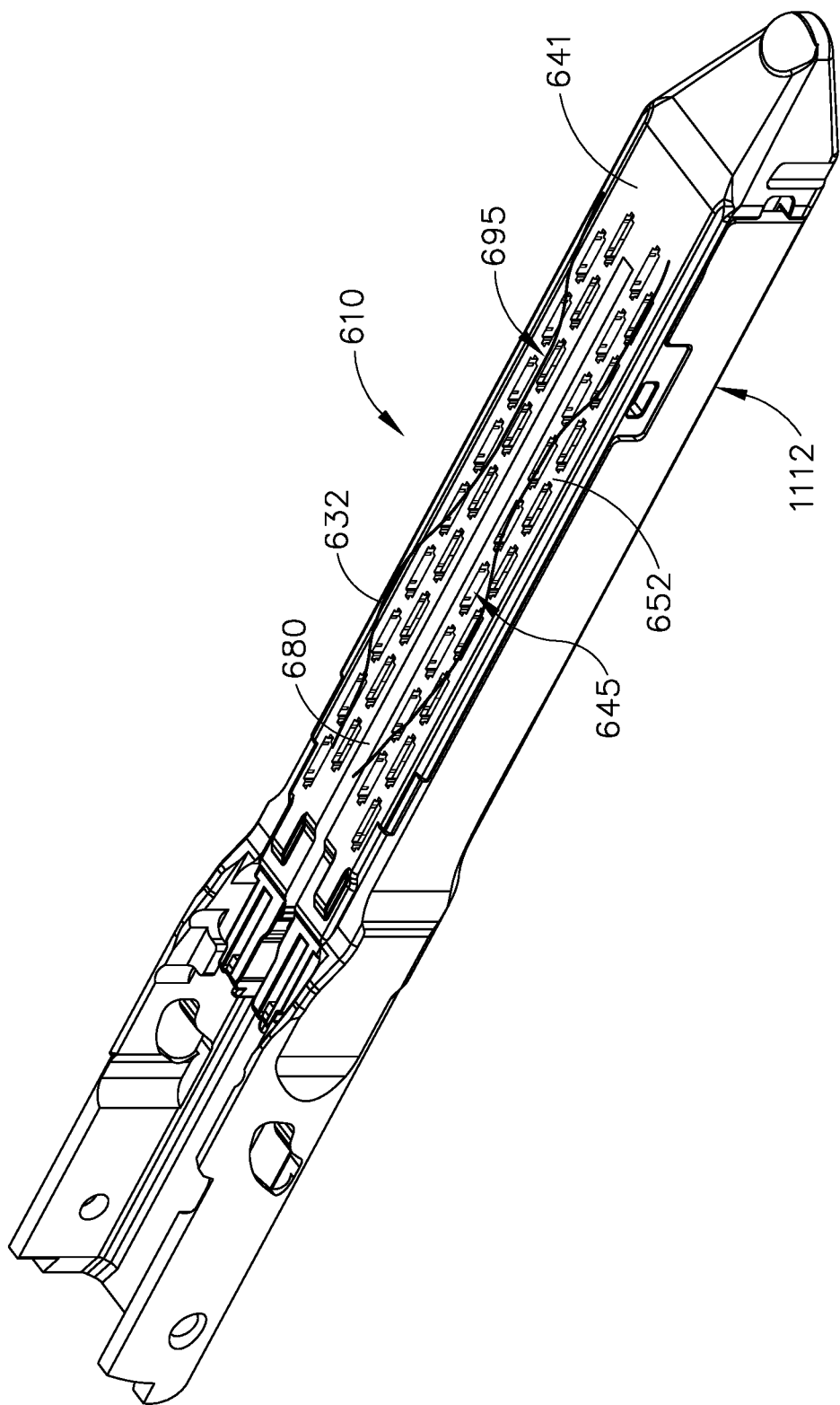
FIG. 15 depicts a perspective view of an exemplary alternative staple cartridge suitable for use in the endocutter stapler of FIG. 7 during performance of the procedure of FIG. 7, including malleable elements secured directly to a deck of the staple cartridge.

B. Exemplary Alternative Staple Cartridge Including Malleable Elements on Staple Cartridge Deck FIG. 15 shows another exemplary alternative staple cartridge (610) inserted in first jaw (1112) of end effector (1110). Staple cartridge (610) is substantially similar to staple cartridge (1140), except that staple cartridge (610) includes two rows of staple cavities (645) on each side of slot (680) of instead of three rows. Therefore, when staple cartridge (610) is incorporated into end effector (1110), two rows of staples (685) are implanted onto opposing, severed portions of tissue rather than three rows of staples (685). Moreover, staple cartridge (610) includes a malleable element (652) on each side of slot (680). As shown in the present example, each malleable element (652) extends in a wave-like configuration from a proximal portion of cartridge deck (641) toward distal end of cartridge deck (641). Particularly, malleable element (652) on each side of slot (680) extends over some of the outer staple cavities (645) (i.e., further from slot (680)) and in between inner cavities (645) (i.e., closer to slot (680)) and outer cavities (645).

In the example shown, each malleable element (652) passes over three of outer cavities (645), but in other examples, each malleable element (652) may extend over fewer cavities (645) than shown, such as two of cavities (645), or more than three cavities (645). Moreover, each malleable element (652) may extend over only outer cavities (645), only inner cavities (645), or a combination of inner and outer cavities (645). In the example shown, each malleable element (652) is removably adhered to cartridge deck (641). However, in other examples, each malleable element (682) may be affixed to cartridge deck (641) by other suitable methods. Other suitable configurations of malleable element (652) will be apparent to persons skilled in the art in view of the teachings herein.

In the example shown, each malleable element (652) is formed entirely of a malleable metal. In other examples, however, each malleable element (652) is formed entirely of a non-metallic malleable material. As yet another merely illustrative example, each malleable element (652) may comprise a combination of a malleable material and a non-malleable material. For example, each malleable element (652) may include a malleable core or portion that is coated with a flexible yet non-malleable material. Alternatively, each malleable element (652) may include a non-malleable core or portion that is coated with a malleable material. Various suitable materials and combinations of materials that may be used to form malleable elements (652) will be apparent to those of ordinary skill in the art in view of the teachings herein. In the present example, the entire length of each malleable element (652) is malleable. However, in some examples, only a portion of the length of each malleable element (652) is malleable. For example, outer portions of malleable elements (652) may be malleable while an inner portion therebetween may be non-malleable. Other suitable configurations of malleable elements (652) will be apparent to persons skilled in the art in view of the teachings herein When staple cartridge (610) is actuated, one of malleable elements (652) will be secured to a first severed portion of tissue (lower colon portion (LC) as shown) by a first set of staples (685), while the other malleable element (652) will be secured to a second severed portion of tissue (the diseased portion (C')) by a second set of staples (685). Particularly, crowns of staples (685) will capture portions of malleable element (652) extending over cavities (645) as staples (685) are driven out of cavities (645) and into contact with tissue, thus pulling malleable element (652) away from cartridge deck (641) and bringing at least a portion of malleable element (652) into contact with tissue.

Figure 18:
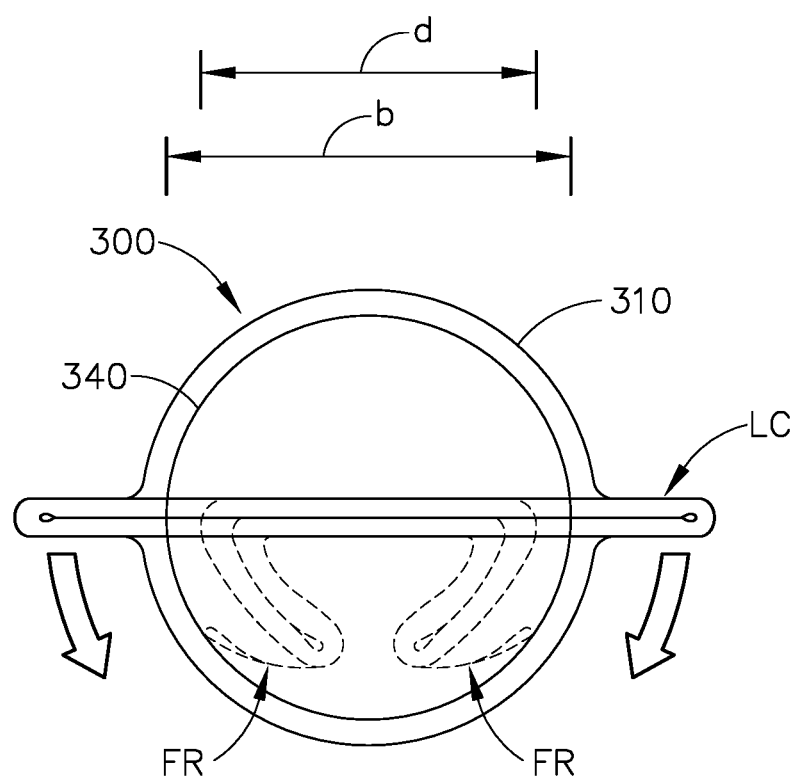
FIG. 18 depicts a top plan view of the portion of the gastrointestinal tract of FIG. 16, with the stapled tissue in a folded configuration.
Figure 19:
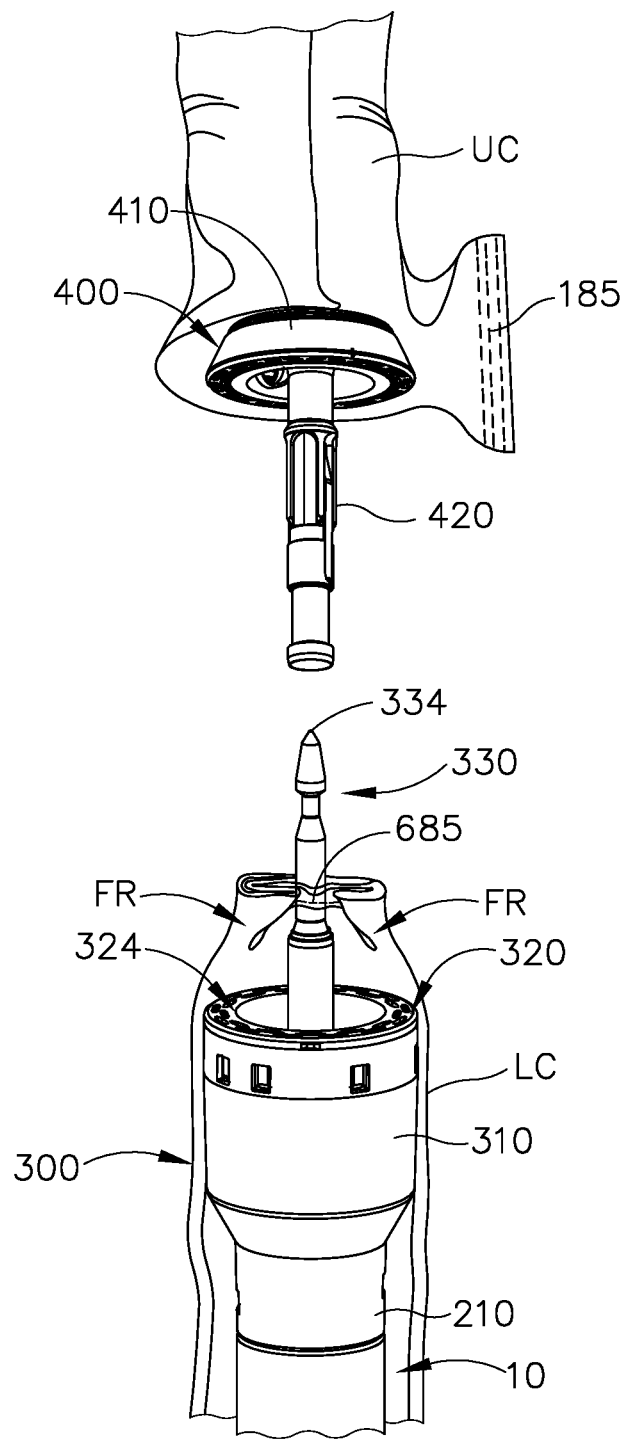
FIG. 19 depicts a schematic view of severed upper and lower portions of a patient's gastrointestinal tract, with the malleable elements of FIG. 15 applied to the severed end of the lower portion of the gastrointestinal tract, showing the anvil of FIG. 3 positioned in the upper portion of the gastrointestinal tract and the stapling head assembly of FIG. 4 positioned in the lower portion of the gastrointestinal tract, during a surgical procedure.

FIGS. 16-19 shows lower colon portion (LC) after surgical system (1000) has been utilized with staple cartridge (610) to staple and sever a portion of lower colon portion (LC). Lower colon portion (LC) therefore includes staples (685) and malleable element (652) coupled thereto in the manner discussed above. In other words, as staples (685) are formed, malleable element (652) is captured amongst the formed staples (685) and coupled to the severed and stapled tissue, as shown in FIGS. 16-19. Malleable element (652) may then be bent to fold the severed and stapled tissue as shown in FIGS. 18-19 and as described in greater detail below, with malleable element (652) maintaining the folded configuration. Various suitable instruments and techniques that may be used to fold the flap regions (FR) of tissue and malleable element (652) will be apparent to those of ordinary skill in the art in view of the teachings herein.

Figure 16:
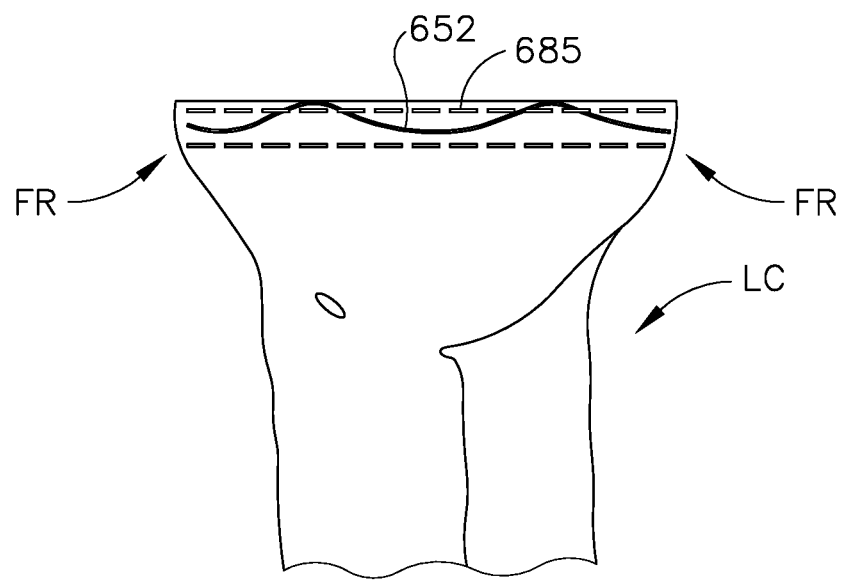
FIG. 16 depicts a side elevational view showing a portion of the gastrointestinal tract after having been stapled and severed utilizing the staple cartridge of FIG. 15, with the stapled tissue in an unfolded configuration.
Figure 17:
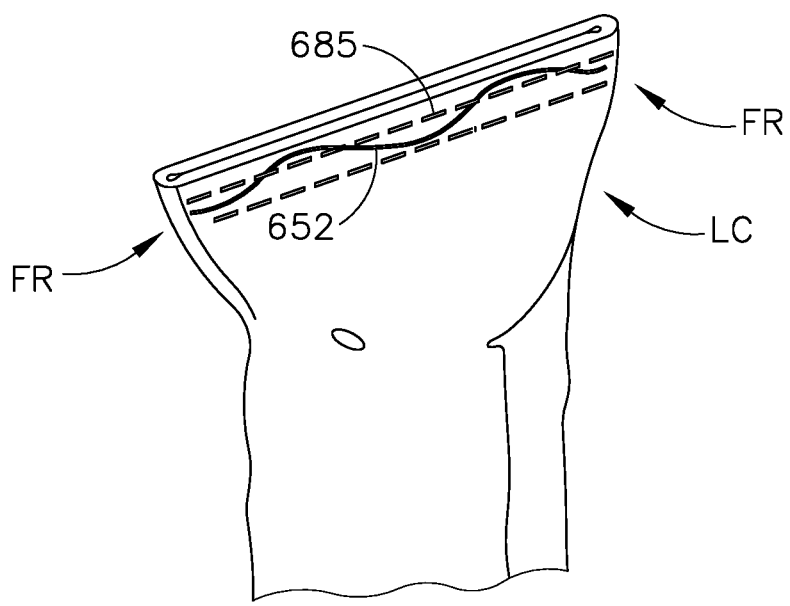
FIG. 17 depicts a perspective view showing the portion of the gastrointestinal tract of FIG. 16, with the stapled tissue in an unfolded configuration.

FIG. 16 shows a step of an anastomosis procedure similar to the steps shown in FIGS. 8 and 14A. Particularly, upper colon portion (UC) and lower colon portion (LC) are shown to have been severed and stapled in a similar manner to that shown in FIGS. 7-8 and 14A-14B. However, at least the lower colon portion (LC) has been severed and stapled utilizing staple cartridge (610). Lower colon portion (LC) therefore includes staples (685) and malleable element (652) coupled thereto in the manner discussed above.

As shown, a portion of shaft (210) and stapling head assembly (300) are inserted into the rectum (R) of the patient and into the lower portion of the colon (C). In the example shown, trocar (330) is inserted through the line of staples (685) such that trocar (330) is exposed out of lower colon portion (LC). Anvil (400) is shown to be positioned in the upper portion (UC) of the colon (C), with shank (420) extending through an opening of the upper colon portion (UC). The flap regions (FR) and other portions of lower colon portion (LC) are shown to be folded radially inwardly toward trocar (330), resulting in staples (685), malleable element (652), and the associated flap regions (FR) all being positioned within the cylindrical plane defined by knife member (340), as shown in FIG. 19, such that the tissue defines an effective width (d) that is smaller than the diameter (b) of knife member (340).

With malleable member (652) holding the severed tissue and staples (685) in the folded configuration to secure flap regions (FR) in an inwardly folded configuration, the operator then connects shank (420) to trocar (330) in the manner discussed above. Alternatively, the operator may fold of flap regions (FR) inwardly after shank (420) and trocar (330) are coupled to one another. The operator may then draw anvil (400) toward stapling head assembly (300), in the manner described above (e.g., utilizing knob (130)), thus also drawing the upper colon portion (UC) toward the lower colon portion (LC). The operator may then retract trocar (330) until the tissue of the upper colon portion (UC) and the lower colon portion (LC) are compressed against the deck member (320) to achieve a desirable gap distance, as discussed above.

The operator may then actuate trigger (150) to actuate stapling head assembly (300), resulting in the stapling and severing of tissue in a similar manner as shown in FIG. 9 to form an anastomosis (A). However, due to the position of the applied staples (685) and all of the tissue at the severed end of lower colon portion (LC) being radially inward of the cut line of circular knife (340) as discussed above, all of the tissue in which staples (685) are applied is severed and no staples (685) are disposed in the tissue that remains at the resulting anastomosis (A) site. Moreover, staples (685) do not impede the successful operation of circular stapler (10), and there are no flap regions (FR) extending outwardly from the anastomosis (A) site. The severed portion of tissue including staples (685) may be removed by the user via the patient's rectum.

Figure 20:
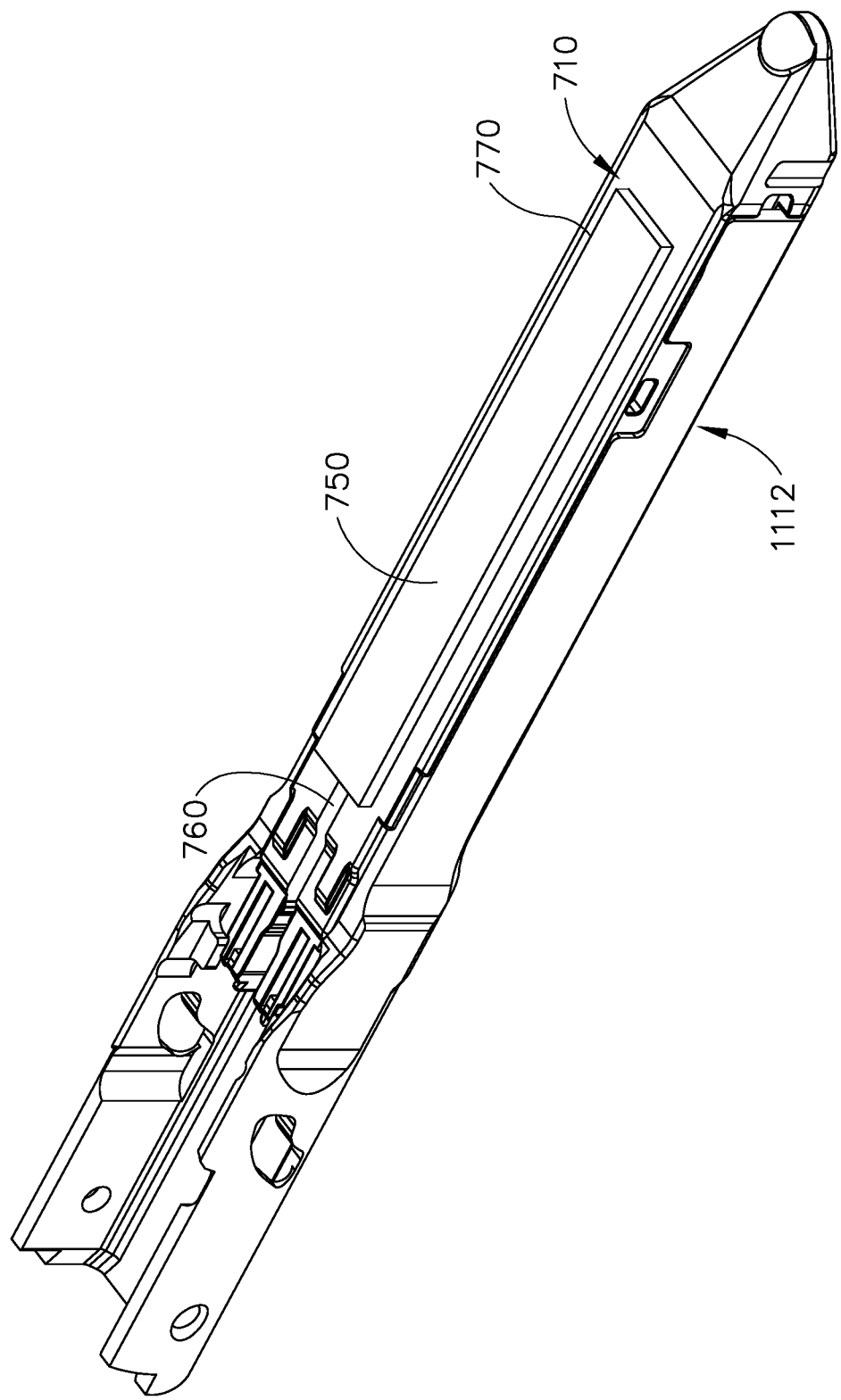
FIG. 20 depicts a perspective view of an exemplary alternative staple cartridge suitable for use in the endocutter stapler of FIG. 7 during performance of the procedure of FIG. 7, including an elastic buttress secured to a deck of the staple cartridge.

C. Exemplary Alternative Staple Cartridge Including Buttress with Elastic Properties FIG. 20 shows another exemplary alternative staple cartridge (710) that may be inserted into first jaw (1112) of end effector (1110) and used during the act of separating the diseased portion (C') of the colon (C) from the lower portion (LC) of the colon (C) as described above with reference to FIG. 7. Staple cartridge (710) is substantially similar to staple cartridge (1140), except for that staple cartridge (710) includes two rows of staple cavities (not shown) on each side of slot (760) of instead of three rows. Therefore, when staple cartridge (710) is incorporated into endocutter stapler (1000), two rows of staples (785) are implanted onto opposing, severed portions of tissue rather than three rows of staples (785).

Figure 21:
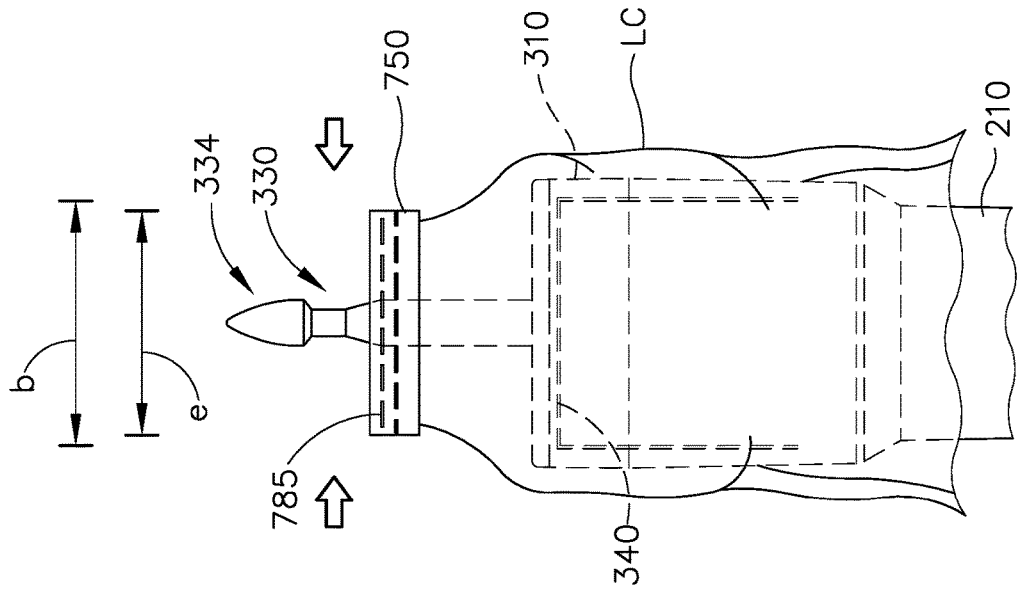
FIG. 21 depicts a side elevational view showing a portion of the gastrointestinal tract after having been stapled and severed utilizing the staple cartridge of FIG. 20, with the buttress and stapled tissue in a non-contracted configuration.
Figure 22:
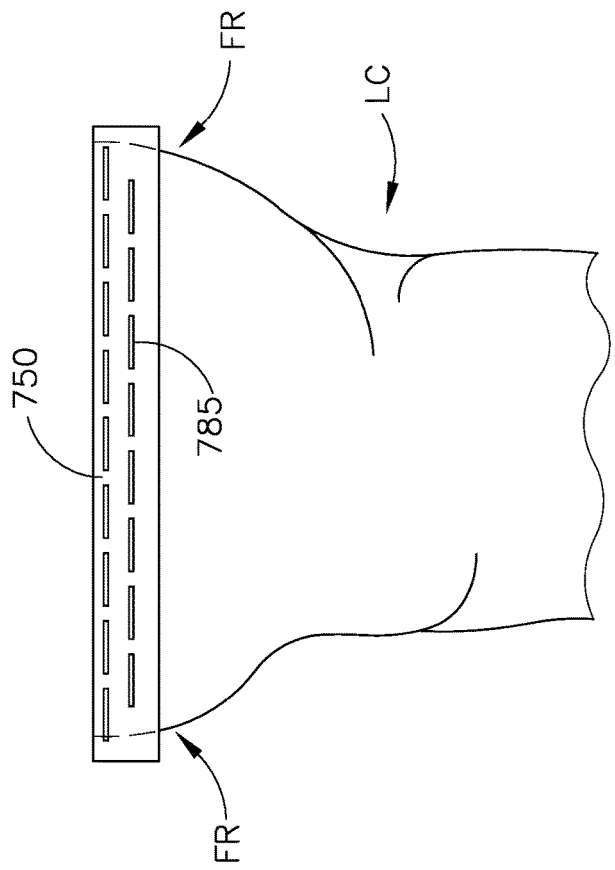
FIG. 22 depicts a side elevational view showing a portion of the gastrointestinal tract of FIG. 21 after having been stapled and severed utilizing the staple cartridge of FIG. 20, with the buttress and stapled tissue in a contracted configuration, and with a shaft of the circular stapler of FIG. 1 positioned in the lower portion of the gastrointestinal tract.

Staple cartridge (710) of the present example further includes a buttress (750) that is secured to deck (770). Buttress (750) is configured to be severed in half by a cutting element that traverses slot (760) during actuation of staple cartridge (710). Buttress (750) of the present example comprises an elastic material that is resiliently biased to transition from an expanded length (as shown in FIGS. 20-21) to a contracted length (as shown in FIG. 22). In the present example, buttress (750) comprises a material (e.g., fabric) with elastic properties, such as Lycra, nylon, etc. In some examples, the entire body of buttress (750) is made of an elastic material. However, in other examples, buttress (750) comprises non-elastic materials with elastic materials coupled thereto which impart elastic properties onto the non-elastic materials. For example, buttress (750) may comprise a non-elastic fabric with elastic members woven into or otherwise coupled to the non-elastic fabric. Other suitable manners of imparting elasticity to buttress (750) will be apparent to persons skilled in the art in view of the teachings herein. By way of example only, the body of buttress (750) may be formed by a mesh of woven material that is provided in the form of a thin sheet. Alternatively, buttress (750) may have any other suitable form.

In the example shown, buttress (750) is removably adhered to deck (770), but in other examples buttress (750) may be associated with or coupled to cartridge (710) in a different manner (e.g., via clips, via hook and loop fasteners, etc.). It should be understood that buttress (750) will be under tension when buttress (750) is secured to deck (770), since buttress (750) is stretched against its own bias when secured to deck (770) and buttress (750) is biased to contract to a shorter length. When an end effector (1110) that incorporates staple cartridge (710) is actuated, buttress (750) will be severed along slot (760) and stapled onto tissue along with staples (785), as shown best in FIG. 21. In particular, FIGS. 21-24 show lower colon portion (LC) after surgical system (1000) has been utilized with staple cartridge (710) to staple and sever a portion of lower colon portion (LC). Lower colon portion (LC) therefore includes staples (785) and buttress (750) coupled thereto in the manner discussed above. In other words, as staples (785) are formed, buttress (750) is captured amongst the formed staples (785) and coupled to the severed and stapled tissue. When buttress (750) is released from deck (770), buttress (750) is no longer being held in tension. Buttress (750) is thus free to contract to a reduced length as shown in FIG. 22. It should be understood that buttress (750) may contract rapidly from the configuration shown in FIG. 21 to the configuration shown in FIG. 22 after being released from deck (770).

Figure 23:
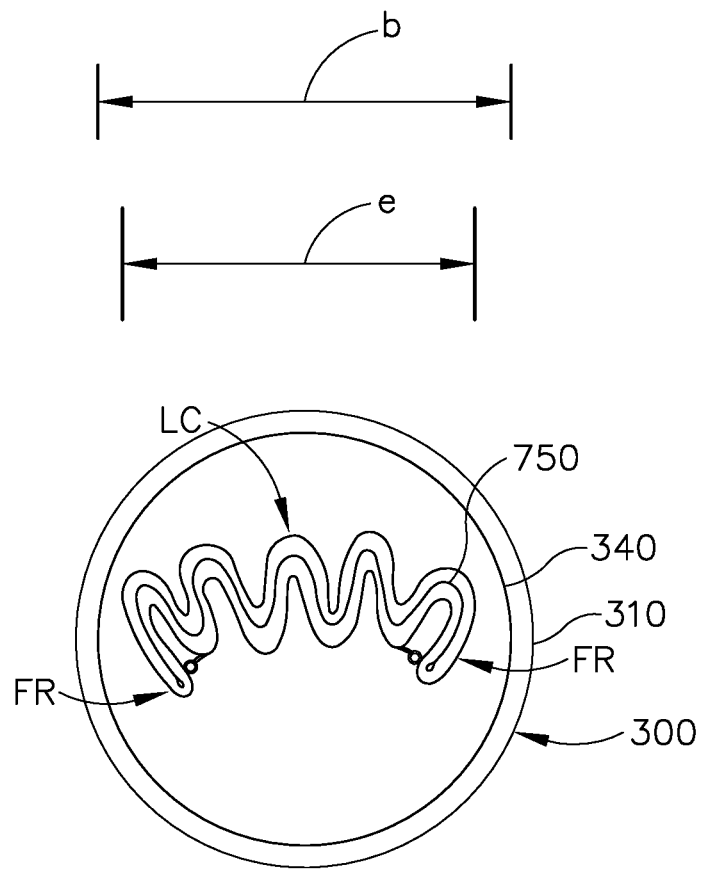
FIG. 23 depicts a top plan view of the portion of the gastrointestinal tract of FIG. 21 in the contracted position.

FIG. 24 shows a step of an anastomosis procedure similar to the steps shown in FIGS. 8 and 14A. Particularly, upper colon portion (UC) and lower colon portion (LC) are shown to have been severed and stapled in a similar manner to that shown in FIGS. 7-8 and 14A-14B. However, at least the lower colon portion (LC) has been severed and stapled utilizing staple cartridge (710). Lower colon portion (LC) therefore includes staples (785) and buttress (750) coupled thereto in the manner discussed above. As shown, a portion of shaft (210) and stapling head assembly (300) are inserted into the rectum (R) of the patient and into the lower portion (LC) of the colon (C). In the example shown, trocar (330) is inserted through the line of staples (785) such that trocar (330) is exposed out of lower colon portion (LC). Anvil (400) is shown to be positioned in the upper portion (UC) of the colon (C), with shank (420) extending through an opening of the upper colon portion (UC). The flap regions (FR) and other portions of lower colon portion (LC) are shown to be drawn radially inwardly toward trocar (330) under the resilient bias imparted by buttress (750), resulting in staples (785), buttress (750), and the associated flap regions (FR) all being positioned within the cylindrical plane defined by knife member (340), as shown in FIGS. 23-24, such that the tissue defines an effective width (e) that is smaller than the diameter (b) of knife member (340).

With buttress (750) holding the severed tissue and staples (785) in the contracted configuration to secure flap regions (FR) in an inwardly drawn configuration, the operator then connects shank (420) to trocar (330) in the manner discussed above. The operator may then draw anvil (400) toward stapling head assembly (300), in the manner described above (e.g., utilizing knob (130)), thus also drawing the upper colon portion (UC) toward the lower colon portion (LC). The operator may then retract trocar (330) until the tissue of the upper colon portion (UC) and the lower colon portion (LC) are compressed against the deck member (320) to achieve a desirable gap distance, as discussed above.

The operator may then actuate trigger (150) to actuate stapling head assembly (300), resulting in the stapling and severing of tissue in a similar manner as shown in FIG. 9 to form an anastomosis (A). However, due to the position of the applied staples (785) and all of the tissue at the severed end of lower colon portion (LC) being radially inward of the cut line of circular knife (340) as discussed above, all of the tissue in which staples (785) are applied is severed and no staples (785) are disposed in the tissue that remains at the resulting anastomosis (A) site. Moreover, staples (785) do not impede the successful operation of circular stapler (10), and there are no flap regions (FR) extending outwardly from the anastomosis (A) site. The severed portion of tissue including staples (785) may be removed by the user via the patient's rectum.

Figure 25:
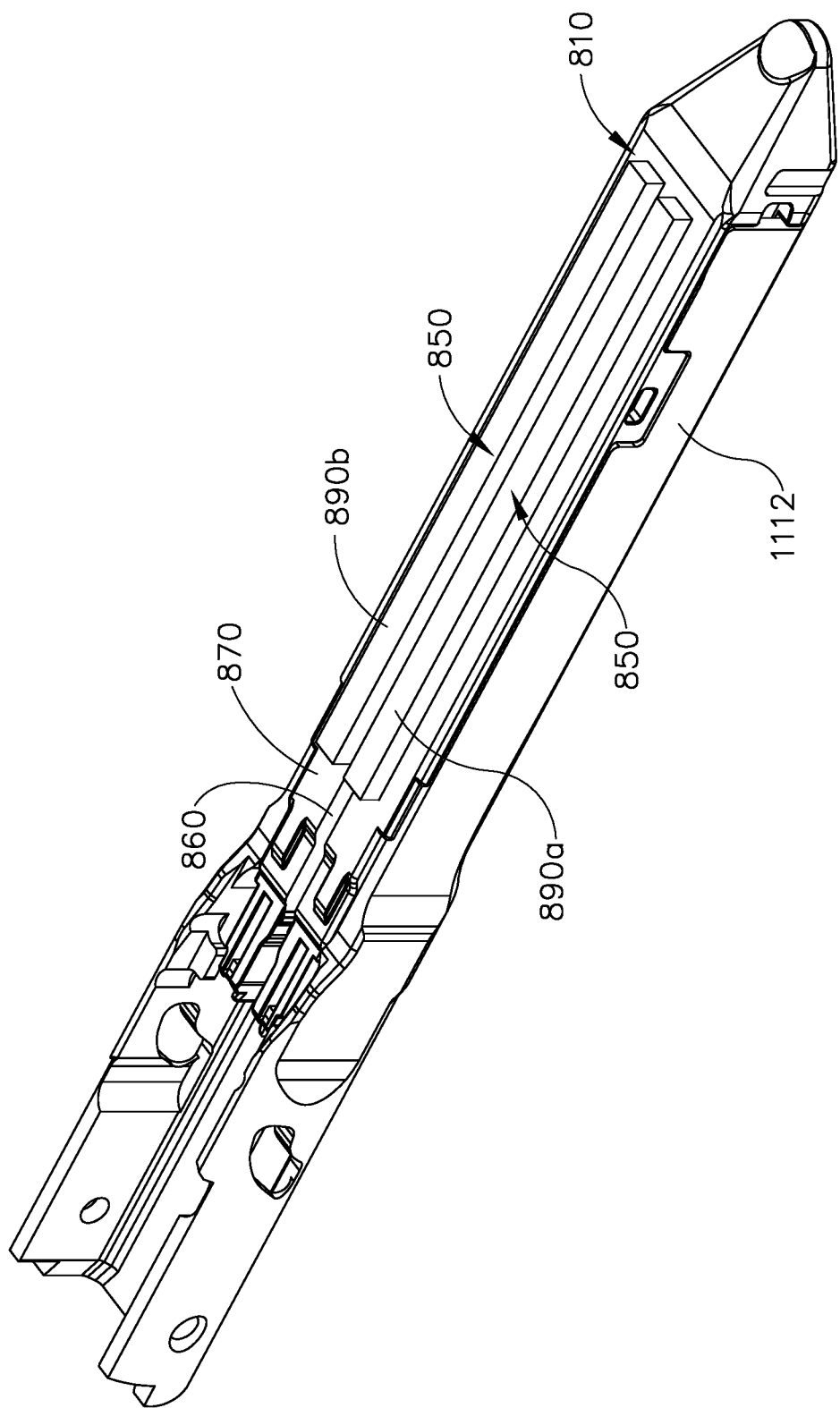
FIG. 25 depicts a perspective view of an exemplary alternative staple cartridge suitable for use in the endocutter stapler of FIG. 7 during performance of the procedure of FIG. 7, including a pair of elastic buttresses secured to a deck of the staple cartridge.

D. Exemplary Alternative Staple Cartridge Including Buttress with Shape Memory Characteristics FIG. 25 shows another exemplary alternative staple cartridge (810) that may be inserted into first jaw (1112) of end effector (1110) and used during the act of separating the diseased portion (C') of the colon (C) from the lower portion (LC) of the colon (C) as described above with reference to FIG. 7. Staple cartridge (810) is substantially similar to staple cartridge (1140), except for that staple cartridge (810) includes two buttresses (850) that are removably secured to a deck (870) of cartridge (810) on each side of slot (860). In other examples, however, rather than having two buttresses (850), there may be only one buttress (850). For instance, a single buttress (850) that spans across the full width of deck (870) may be severed in half by a cutting element that traverses slot (860) during actuation of staple cartridge (810). Various suitable forms that the body of buttress (850) may take will be apparent to those of ordinary skill in the art in view of the teachings herein.

By way of example only, the body of buttress (850) may be formed by a mesh of woven material that is provided in the form of a thin sheet. In the present example, buttresses (850) include shape memory characteristics, discussed in detail below. The shape memory characteristics of buttresses (850) resiliently bias each buttress (850) to assume a non-flat, "U" shaped configuration. In the examples shown or in other examples, the shape memory characteristics of buttresses (850) may be imparted to buttresses (850) in various ways. In some examples, each buttress (850) may be comprised entirely of a shape memory material. In other examples, however, each buttress (850) comprise a combination of non-shape memory materials and shape memory materials (e.g., a nitinol wire or band) coupled thereto which impart shape memory properties to buttress (850). Other suitable manners of imparting shape memory characteristics to buttress (850) will be apparent to persons skilled in the art in view of the teachings herein.

Figure 26:
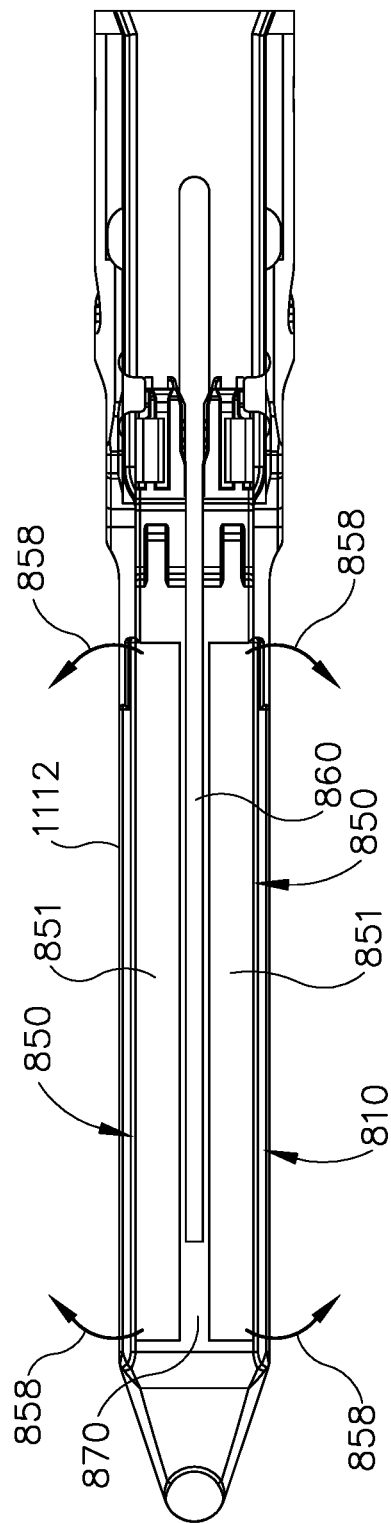
FIG. 26 depicts a top plan view of the staple cartridge of FIG. 25, in which the buttresses are biased in the direction of the arrows.
Figure 27:
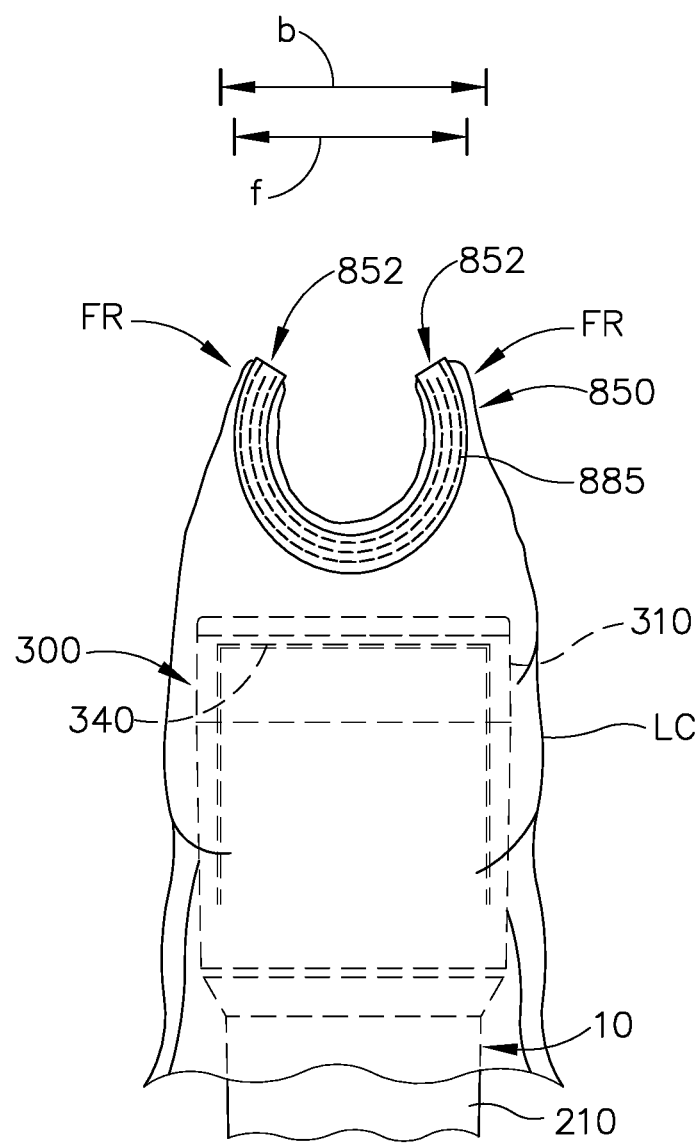
FIG. 27 depicts a side elevational view showing a portion of the gastrointestinal tract after having been stapled and severed utilizing the staple cartridge of FIG. 25, with the stapled tissue in a contracted configuration.

In the example shown, each buttress (850) is removably adhered to deck (870), but in other examples each buttress (850) may be associated with or coupled to cartridge (810) in a different manner (e.g., via clips, via hook and loop fasteners, etc.). It should be understood that each buttress (850) will be under stress when buttress (850) is secured to deck (870), since each buttress (850) is deformed to achieve a flat configuration when secured to deck (870). When an end effector (1110) that incorporates staple cartridge (810) is actuated, each buttress (850) will be stapled onto tissue along with staples (885), as shown best in FIG. 27. In particular, FIG. 27 shows lower colon portion (LC) after surgical system (1000) has been utilized with staple cartridge (810) to staple and sever a portion of lower colon portion (LC). Lower colon portion (LC) therefore includes staples (885) and buttress (850) coupled thereto in the manner discussed above. In other words, as staples (885) are formed, buttress (850) is captured amongst the formed staples (885) and coupled to the severed and stapled tissue. When buttress (850) is released from deck (870), buttress (850) is no longer being held in a stressed state. Buttress (850) is thus free to assume its natural "U" shaped configuration as shown in FIG. 27. It should be understood that buttress (850) may contract rapidly from the configuration shown in FIGS. 25-26 to the configuration shown in FIG. 26 after being released from deck (870).

In the present example, each buttress (850) is biased to assume a "U" shape that is oriented along the same plane along which the faces (851) of buttress (850) extend. Thus, when buttress (850) is stapled onto tissue along with staples (885), buttress (850) assumes a "U" shape and thereby forces the stapled tissue to assume the "U" shape. FIG. 26 shows arrows (858) indicating the direction in which buttresses (850) will deform when released from deck (870). Arrows (858) are coplanar with buttresses (850) and extend transversely relative to the longitudinal axis of each buttress (850). Thus, when buttress (850) is stapled onto tissue along with staples (885), the shape memory of buttress (850) will pull the flap regions (FR) inwardly toward each other and toward the longitudinal axis of the colon (C) and trocar (330), with the flap regions (FR) and the ends (852) of buttress (850) all lying on planes that are parallel to the plane defined by face (851) of buttress (850).

After staple cartridge (810) has been actuated and buttress (850) and staples (858) applied to the tissue, trocar (330) is inserted through the line of staples (885) such that trocar (330) is exposed out of lower colon portion (LC). As shown in FIG. 27, end portions (852) of buttress (850) face away from stapling head assembly (300). This results in staples (885), buttress (850), and the associated flap regions (FR) being positioned within the cylindrical plane defined by knife member (340), such that the tissue defines an effective width (f) that is smaller than the diameter (b) of knife member (340), as shown in FIG. 27.

With buttress (850) holding the severed tissue and staples (885) in the contracted configuration to secure flap regions (FR) in an inwardly drawn configuration, the operator then connects shank (420) to trocar (330) in the manner discussed above. The operator may then draw anvil (400) toward stapling head assembly (300), in the manner described above (e.g., utilizing knob (130)), thus also drawing the upper colon portion (UC) toward the lower colon portion (LC). The operator may then retract trocar (330) until the tissue of the upper colon portion (UC) and the lower colon portion (LC) are compressed against the deck member (320) to achieve a desirable gap distance, as discussed above.

The operator may then actuate trigger (150) to actuate stapling head assembly (300), resulting in the stapling and severing of tissue in a similar manner as shown in FIG. 9 to form an anastomosis (A). However, due to the position of the applied staples (885) and all of the tissue at the severed end of lower colon portion (LC) being radially inward of the cut line of circular knife (340) as discussed above, all of the tissue in which staples (885) are applied is severed and no staples (885) are disposed in the tissue that remains at the resulting anastomosis (A) site. Moreover, staples (885) do not impede the successful operation of circular stapler (10), and there are no flap regions (FR) extending outwardly from the anastomosis (A) site. The severed portion of tissue including staples (885) may be removed by the user via the patient's rectum.

Figure 28:
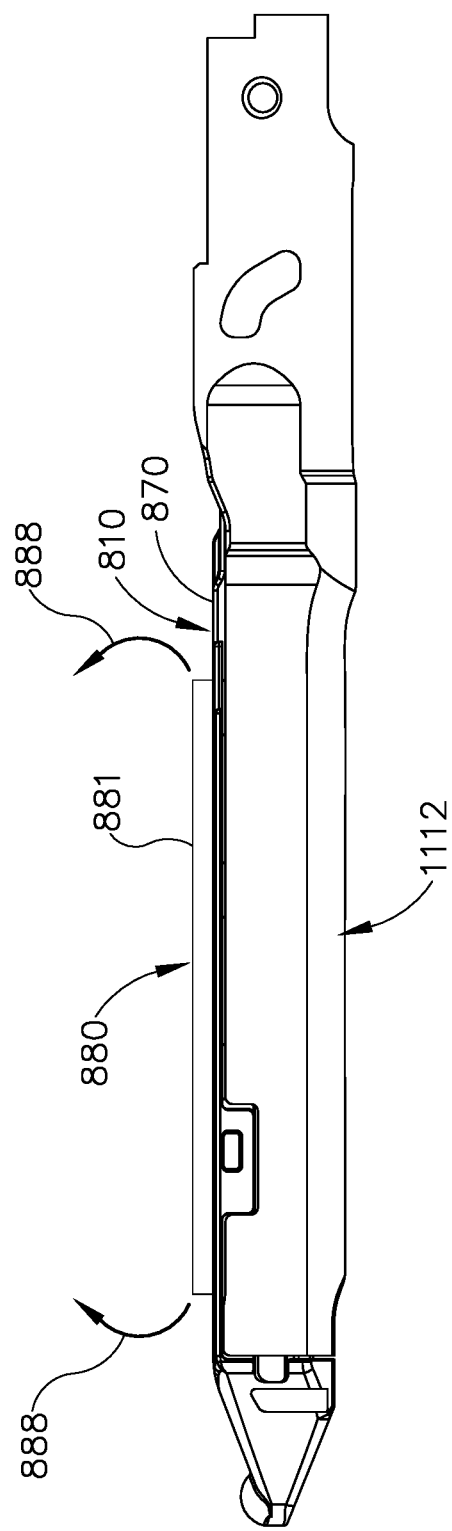
FIG. 28 depicts a side elevational view of an exemplary alternative staple cartridge suitable for use in the endocutter stapler of FIG. 7 during performance of the procedure of FIG. 7, including a pair of elastic buttresses secured to a deck of the staple cartridge, in which the buttresses are biased in the direction of the arrows.
Figure 29:
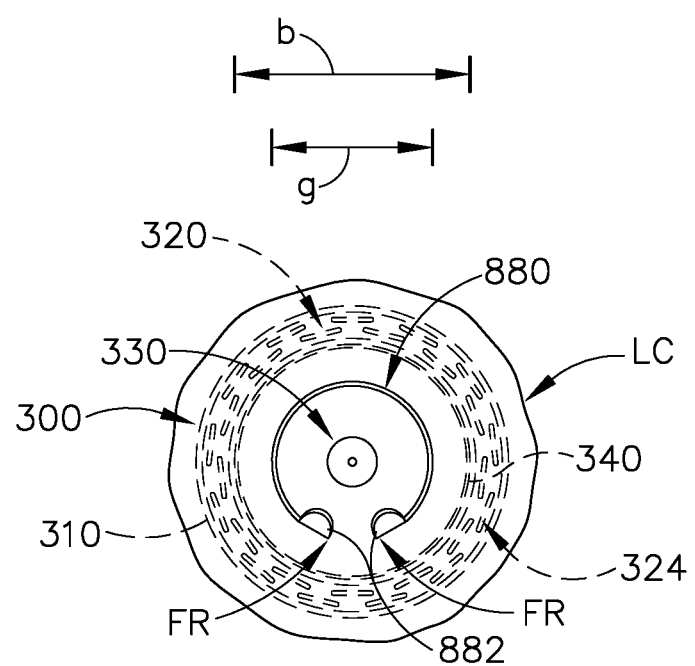
FIG. 29 depicts a top plan view showing a portion of the gastrointestinal tract after having been stapled and severed utilizing the staple cartridge of FIG. 28, with the stapled tissue in a contracted configuration.

FIGS. 28-29 show a merely illustrative variation of staple cartridge (810). In this version, staple cartridge (810) includes a pair of buttresses (880) that are configured and operable identically to buttresses (850) except that buttresses (880) in this example are biased to return to a "U" shape along paths (888) that are different from paths (858) of buttresses (850). In particular, FIG. 28 shows arrows (888) indicating the direction in which buttresses (880) will deform when released from deck (870). Arrows (888) are perpendicular to buttresses (850) and extend transversely relative to the longitudinal axis of each buttress (850). In particular, arrows (888) extend along a plane that is normal to the face (881) of buttress (880). When buttress (880) is stapled onto tissue along with staples (885) as shown in FIG. 29, the shape memory of buttress (880) will pull the flap regions (FR) inwardly toward each other and around the longitudinal axis of the colon (C) and trocar (330), with the flap regions (FR) and ends (882) of buttress (880) all lying on planes that are perpendicular to the plane defined by face (881) of buttress (880).

Staples (885) and associated tissue thus extend around trocar (330) in a concentric manner. Similar to the other examples described herein, this results in staples (885), buttress (880), and the associated flap regions (FR) being positioned within the cylindrical plane defined by knife member (340), as shown in FIG. 29, such that the tissue defines an effective width (g) that is smaller than the diameter (b) of knife member (340). Thus, when the operator actuates stapling head assembly (300) to staple and sever tissue in a similar manner as shown in FIG. 9 to form an anastomosis (A), due to the position of the applied staples (885) and all of the tissue at the severed end of lower colon portion (LC) being radially inward of the cut line of circular knife (340) as discussed above, all of the tissue in which staples (885) are applied is severed and no staples (885) are disposed in the tissue that remains at the resulting anastomosis (A) site. Moreover, staples (885) do not impede the successful operation of circular stapler (10), and there are no flap regions (FR) extending outwardly from the anastomosis (A) site.

E. Exemplary Alternative Staple Cartridge Including Buttress with Grommets

Figure 30:
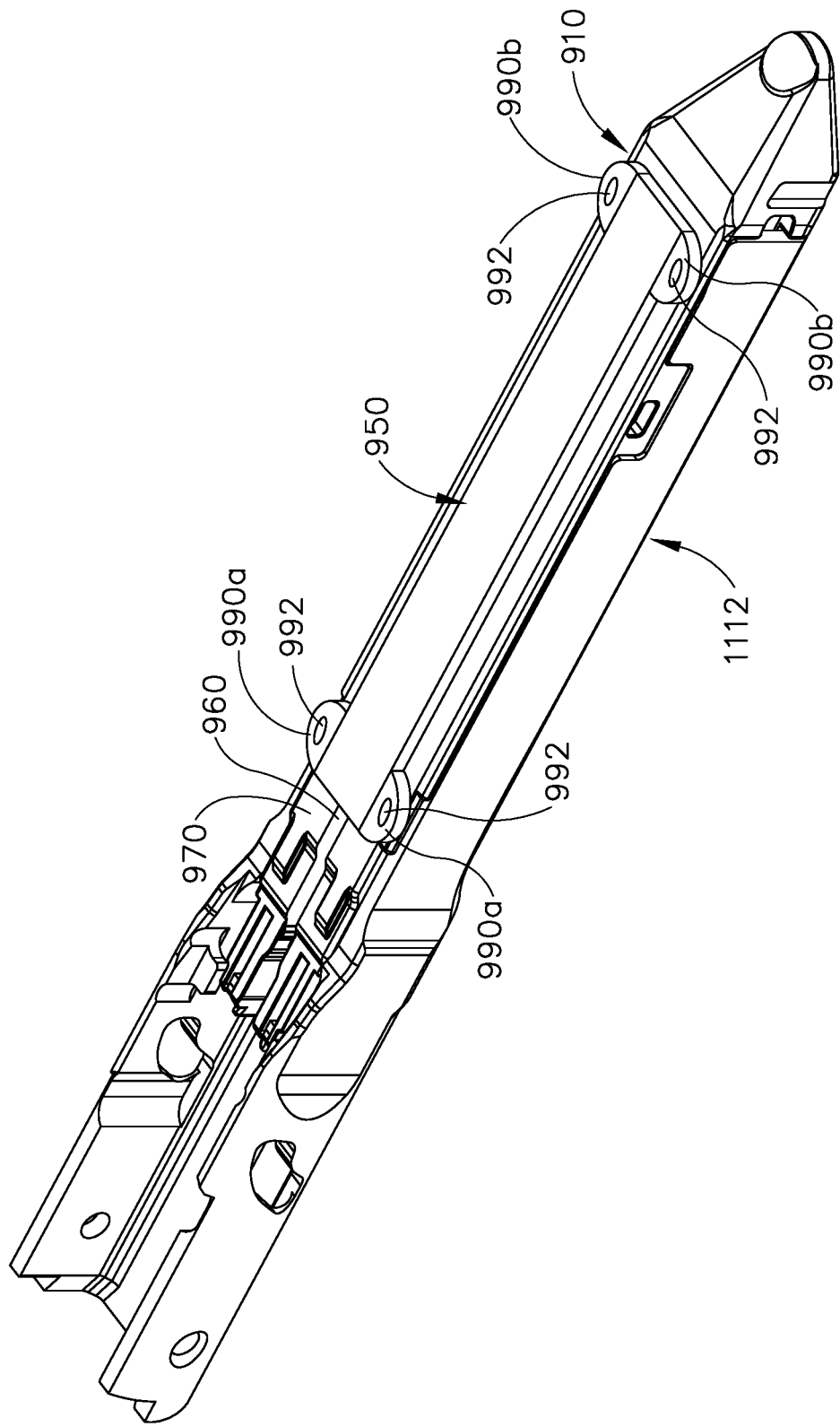
FIG. 30 depicts a perspective view of an exemplary alternative staple cartridge suitable for use in the endocutter stapler of FIG. 7 during performance of the procedure of FIG. 7, including a buttress with grommets secured to a deck of the staple cartridge.

FIG. 30 shows another exemplary alternative staple cartridge (910) that may be inserted into first jaw (1112) of end effector (1110) and used during the act of separating the diseased portion (C') of the colon (C) from the lower portion (LC) of the colon (C) as described above with reference to FIG. 7. Staple cartridge (910) is substantially similar to staple cartridge (1140), except for that staple cartridge (910) includes two rows of staple cavities (not shown) on each side of slot (960) of instead of three rows. Therefore, when staple cartridge (910) is incorporated into endocutter stapler (1000), two rows of staples (985) are implanted onto opposing, severed portions of tissue rather than three rows of staples (985).

Staple cartridge (910) of the present example further includes a buttress (950) that is secured to deck (970). Buttress (950) is configured to be severed in half by a cutting element that traverses slot (960) during actuation of staple cartridge (910). Buttress (950) of the present example comprises an integral pair of proximal grommets (990a) and an integral pair of distal grommets (990b). Grommets (990a, 990b) are formed as laterally extending members (i.e., extending laterally away from slot (960)) with reinforced openings (992). By way of example only, the body of buttress (950) may be formed by a mesh of woven material that is provided in the form of a thin sheet. Alternatively, buttress (950) may have any other suitable form.

Figure 31:
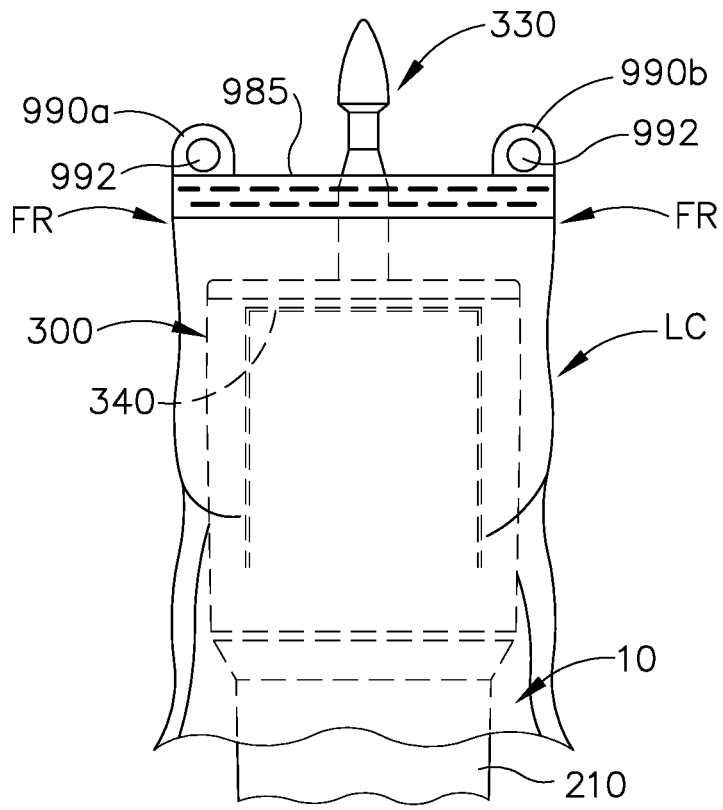
FIG. 31 depicts a side elevational view showing a portion of the gastrointestinal tract after having been stapled and severed utilizing the staple cartridge of FIG. 30, with the buttress and the stapled tissue in an unfolded configuration.
Figure 32:
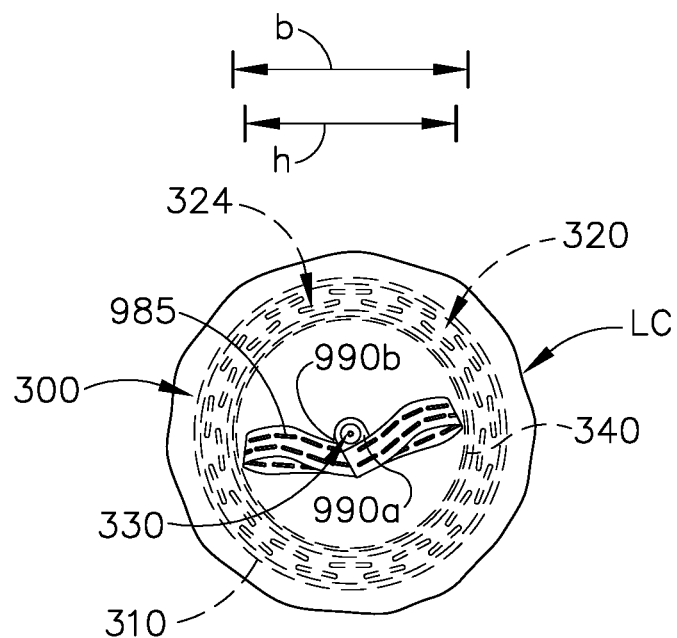
FIG. 32 depicts a top plan view showing a portion of the gastrointestinal tract after having been stapled and severed utilizing the staple cartridge of FIG. 30, with the buttress and the stapled tissue in a folded configuration.

In the example shown, buttress (950) is removably adhered to deck (970), but in other examples buttress (950) may be associated with or coupled to cartridge (910) in a different manner (e.g., via clips, via hook and loop fasteners, etc.). When an end effector (1110) that incorporates staple cartridge (910) is actuated, buttress (950) will be severed along slot (960) and stapled onto tissue along with staples (985), as shown best in FIG. 31. In particular, FIGS. 31-33 show lower colon portion (LC) after surgical system (1000) has been utilized with staple cartridge (910) to staple and sever a portion of lower colon portion (LC). Lower colon portion (LC) therefore includes staples (985) and buttress (950) coupled thereto in the manner discussed above. In other words, as staples (985) are formed, buttress (950) is captured amongst the formed staples (985) and coupled to the severed and stapled tissue.

When buttress (950) is released from deck (970), grommets (990a, 990b) extend distally from the severed end of lower colon portion (LC), as shown in FIG. 31. The operator may then grasp each grommet (990a, 990b) and manipulate buttress (950) and the tissue to pass trocar (330) through opening (992) of each grommet (990a, 990b). It should be understood that openings (992) are perpendicular to the longitudinal axis of trocar (330) in the stage shown in FIG. 31, such that the operator must twist and fold flap regions (FR) in order to pass trocar (330) through openings (992). This results in flap regions (FR) being drawn inwardly as shown in FIG. 32. This results in staples (985), buttress (950), and the associated flap regions (FR) all being positioned within the cylindrical plane defined by knife member (340), such that the tissue defines an effective width (h) that is smaller than the diameter (b) of knife member (340).

FIG. 33 shows a step of an anastomosis procedure similar to the steps shown in FIG. 8. Particularly, upper colon portion (UC) and lower colon portion (LC) are shown to have been severed and stapled in a similar manner to that shown in FIGS. 7-8. However, at least the lower colon portion (LC) has been severed and stapled utilizing staple cartridge (910). Lower colon portion (LC) therefore includes staples (985) and buttress (950) coupled thereto in the manner discussed above. As shown, a portion of shaft (210) and stapling head assembly (300) are inserted into the rectum (R) of the patient and into the lower portion (LC) of the colon (C). In the example shown, trocar (330) is inserted through the line of staples (985) such that trocar (330) is exposed out of lower colon portion (LC). Anvil (400) is shown to be positioned in the upper portion (UC) of the colon (C), with shank (420) extending through an opening of the upper colon portion (UC). The flap regions (FR) and other portions of lower colon portion (LC) are then twisted and folded over in order to pass trocar (330) through openings (992) of grommets (990a, 990b) as described above, resulting in staples (985), buttress (950), and the associated flap regions (FR) all being positioned within the cylindrical plane defined by knife member (340) as shown in FIGS. 32-33, such that the tissue defines an effective width (h) that is smaller than the diameter (b) of knife member (340).

With buttress (950) holding the severed tissue and staples (985) to trocar (330) configuration to secure flap regions (FR) in an inwardly folded configuration, the operator then connects shank (420) to trocar (330) in the manner discussed above. The operator may then draw anvil (400) toward stapling head assembly (300), in the manner described above (e.g., utilizing knob (130)), thus also drawing the upper colon portion (UC) toward the lower colon portion (LC). The operator may then retract trocar (330) until the tissue of the upper colon portion (UC) and the lower colon portion (LC) are compressed against the deck member (320) to achieve a desirable gap distance, as discussed above. It should be understood that the retraction of trocar (330) and anvil (440) may further draw flap regions (FR) toward the longitudinal axis of trocar (330), which may thus further reduce the effective width (h) of staples (985), buttress (950), and the associated flap regions (FR).

The operator may then actuate trigger (150) to actuate stapling head assembly (300), resulting in the stapling and severing of tissue in a similar manner as shown in FIG. 9 to form an anastomosis (A). However, due to the position of the applied staples (985) and all of the tissue at the severed end of lower colon portion (LC) being radially inward of the cut line of circular knife (340) as discussed above, all of the tissue in which staples (985) are applied is severed and no staples (985) are disposed in the tissue that remains at the resulting anastomosis (A) site. Moreover, staples (985) do not impede the successful operation of circular stapler (10), and there are no flap regions (FR) extending outwardly from the anastomosis (A) site. The severed portion of tissue including staples (785) may be removed by the user via the patient's rectum.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising a staple cartridge, wherein the staple cartridge comprises (i) a plurality of staples, (ii) a deck, wherein the deck defines a plurality of openings, wherein each opening of the plurality of openings is associated with a corresponding staple of the plurality of staples, such that each staple is configured to pass through a corresponding opening of the plurality of openings, and (iii) a deformable feature, wherein the deformable feature is configured to be coupled to tissue in response to actuation of the staple cartridge, wherein the deformable feature is configured to retain at least one outer portion of stapled tissue in an inwardly directed position relative to an inner portion of stapled tissue.

EXAMPLE 2

The apparatus of Example 1, wherein the staple cartridge further comprises a buttress, wherein the deformable feature is positioned on the buttress.

EXAMPLE 3

The apparatus of Example 2, wherein the deformable feature comprises at least one plastically deformable element associated with the buttress.

EXAMPLE 4

The apparatus of Example 3, wherein the deformable feature comprises a plurality of malleable features disposed on the buttress.

EXAMPLE 5

The apparatus of Example 4, wherein each of the malleable features comprises a metal wire.

EXAMPLE 6

The apparatus of any one or more of Examples 1 through 5, wherein the deformable feature comprises at least one malleable element disposed on the deck.

EXAMPLE 7

The apparatus of Example 6, wherein the malleable element further comprises a metal wire.

EXAMPLE 8

The apparatus of any one or more of Examples 1 through 7, wherein the deformable feature comprises an elastically deformable element.

EXAMPLE 9

The apparatus of Example 8, wherein the deformable feature is configured to transition from a stretched state to a contracted state in response to actuation of the staple cartridge.

EXAMPLE 10

The apparatus of any one or more of Examples 1 through 9, wherein the deformable feature is configured to transition the at least one outer portion of stapled tissue into an inwardly directed position relative to an inner portion of stapled tissue automatically in response to actuation of the staple cartridge.

EXAMPLE 11

The apparatus of any one or more of Examples 1 through 10, wherein the deformable feature is configured to transition the at least one outer portion of stapled tissue into an inwardly directed position relative to an inner portion of stapled tissue in response to bending of the deformable feature.

EXAMPLE 12

The apparatus of Example 11, wherein the deformable feature comprises a shape memory material.

EXAMPLE 13

The apparatus of any of examples 1 through 12, further comprising a circular stapler, wherein the circular stapler comprises: (i) an anvil, and (ii) a stapling head assembly, wherein the stapling head assembly comprises: (A) a rod configured to engage the anvil, (B) a knife member configured to form a circular cut line in tissue, and (C) a staple driver, wherein the anvil and stapling head assembly are configured to cooperate to clamp and staple tissue; wherein the deformable feature is configured to retain at least one outer portion of stapled tissue in an inwardly directed position relative to the rod.

EXAMPLE 14

The apparatus of Example 13, wherein the deformable feature is configured to fold the outer portion of stapled tissue relative to the inner portion of stapled tissue.

EXAMPLE 15

The apparatus of any one or more of Examples 13 through 14, wherein the deformable feature is configured to retain the at least one outer portion of stapled tissue in an inwardly folded position relative to an inner portion of stapled tissue within a circular cut line formed by the knife member.

EXAMPLE 16

The apparatus of any one or more of Examples 1 through 15, further comprising: (a) an end effector, wherein the end effector comprises: (i) an anvil, and (ii) a lower jaw, wherein the anvil is pivotable toward the lower jaw to capture tissue between the anvil and the lower jaw, wherein the staple cartridge is secured to the lower jaw; and (b) a stapling and severing mechanism in communication with the shaft assembly and end effector, wherein the stapling and severing mechanism is configured to sever and staple tissue clamped between the anvil and the lower jaw.

EXAMPLE 17

A method of operating on tissue using a circular stapler, wherein the circular stapler comprises an anvil and a stapling head assembly, wherein the stapling head assembly includes a rod, a knife member, and a staple driver, wherein the knife member is configured to provide a circular cut line, wherein the anvil and the stapling head assembly are configured to cooperate to clamp and staple tissue, wherein the method comprises: (a) severing and stapling a first portion of anatomical structure using a non-circular stapler, thereby leaving a plurality of staples and a deformable feature on a severed end portion of the first portion of anatomical structure; (b) inserting the anvil of the circular stapler into a second portion of anatomical structure; (c) inserting the stapling head assembly into the first portion of anatomical structure until at least a portion of the rod extends past the severed end portion of the first portion of anatomical structure; (d) drawing the deformable member toward the rod, thereby holding the plurality of staples on the severed end portion at a position inward of the cut line of the knife member; (e) coupling the rod and the anvil; (f) clamping the first and second portions of anatomical structure together between the anvil and the sapling head assembly; (g) directing the drivable knife member toward the anvil, thereby severing the severed end portion and the staples from the first portion of anatomical structure and at least part of the second portion of anatomical structure; and (h) stapling the first and second portions of anatomical structure together using the staple driver.

EXAMPLE 18

The method of Example 17, wherein drawing the deformable member toward the rod comprises plastically deforming the deformable feature.

EXAMPLE 19

The method of any one or more of Examples 17 through 18, wherein drawing the deformable member toward the rod comprises elastically deforming the deformable feature.

EXAMPLE 20

A method of operating on tissue using a circular stapler, wherein the circular stapler comprises an anvil and a stapling head assembly, wherein the stapling head assembly includes a rod, a knife member, and a staple driver, wherein the knife member is configured to provide a circular cut line, wherein the anvil and the stapling head assembly are configured to cooperate to clamp and staple tissue, wherein the method comprises: (a) severing and stapling a first portion of the colon using a non-circular stapler, thereby leaving a first plurality of staples and a deformable feature on a first severed end portion of the first portion of the colon; (b) severing and stapling a second portion of the colon using a non-circular stapler, thereby leaving a second plurality of staples on a second severed end portion of the second portion of the colon; (c) inserting the anvil of the circular stapler into the second portion of the colon; (d) inserting the stapling head assembly into the first portion of the colon until at least a portion of the rod extends past the severed end portion of the first portion of the colon; (e) deforming the deformable member, thereby drawing the first severed end portion inward toward the rod such that the first plurality of staples and the first severed end portion lie radially inwardly of the cut line of the knife member; (f) directing the drivable knife member toward the anvil, thereby severing the first severed end portion and the first plurality of staples from the first portion of the patient's colon and at least part of the second portion of the patient's colon; and (g) stapling the first and second portions of the colon together.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, the disclosure of which is incorporated by reference herein; U.S. Pub. No. 2014/0144968, entitled "Surgical Staple with Integral Pledget for Tip Deflection," published May 29, 2014, the disclosure of which is incorporated by reference herein; U.S. Pub. No. 2014/0158747, entitled "Surgical Stapler with Varying Staple Widths along Different Circumferences," published Jun. 12, 2014, the disclosure of which is incorporated by reference herein; U.S. Pub. No. 2014/0144969, entitled "Pivoting Anvil for Surgical Circular Stapler," published May 29, 2014, the disclosure of which is incorporated by reference herein; U.S. Pub. No. 2014/0151430, entitled "Circular Anvil Introduction System with Alignment Feature," published Jun. 5, 2014, the disclosure of which is incorporated by reference herein; U.S. Pub. No. 2014/0166717, entitled "Circular Stapler with Selectable Motorized and Manual Control, Including a Control Ring," published Jun. 19, 2014, the disclosure of which is incorporated by reference herein; U.S. Pub. No. 2014/0166728, entitled "Motor Driven Rotary Input Circular Stapler with Modular End Effector," published Jun. 19, 2014, the disclosure of which is incorporated by reference herein; and/or U.S. Pub. No. 2014/0166718, entitled "Motor Driven Rotary Input Circular Stapler with Lockable Flexible Shaft," published Jun. 19, 2014, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, the disclosure of which is incorporated by reference herein, and/or U.S. Pub. No. 2010/0264193, entitled "Surgical Stapling Instrument with An Articulatable End Effector," published Oct. 21, 2010, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising a staple cartridge, wherein the staple cartridge comprises:
   (i) a plurality of staples,
   (ii) a deck, wherein the deck defines a plurality of openings, wherein each opening of the plurality of openings is associated with a corresponding staple of the plurality of staples, such that each staple is configured to pass through a corresponding opening of the plurality of openings, and
   (iii) a buttress including an elastically deformable feature, wherein the buttress is configured to transition from a stretched state to a subsequent contracted state, wherein in the stretched state the buttress is secured to the deck in tension and the buttress is not yet contacting tissue and first and second jaws of a surgical stapler are separated from one another, with the staple cartridge disposed in one of the jaws of the surgical stapler, wherein in the subsequent contracted state the buttress including the elastically deformable feature is detached from the deck and is coupled to tissue in response to actuation of the staple cartridge, wherein in the subsequent contracted state the elastically deformable feature is configured to retain at least one outer portion of stapled tissue in an inwardly directed position relative to an inner portion of stapled tissue, wherein the buttress is formed from a non-elastic fabric with the elastically deformable feature woven into the non-elastic fabric.

2. The apparatus of claim 1, wherein the elastically deformable feature is configured to transition the at least one outer portion of stapled tissue into the inwardly directed position relative to the inner portion of stapled tissue automatically in response to actuation of the staple cartridge.

3. The apparatus of claim 1, wherein the elastically deformable feature is configured to transition the at least one outer portion of stapled tissue into the inwardly directed position relative to the inner portion of stapled tissue in response to bending of the elastically deformable feature.

4. The apparatus of claim 1, further comprising a circular stapler, wherein the circular stapler comprises:
   (i) an anvil, and
   (ii) a stapling head assembly, wherein the stapling head assembly comprises:
      (A) a rod configured to engage the anvil,
      (B) a knife member configured to form a circular cut line in tissue, and
      (C) a staple driver,
      wherein the anvil and stapling head assembly are configured to cooperate to clamp and staple tissue;
      wherein the elastically deformable feature is configured to retain the at least one outer portion of stapled tissue in the inwardly directed position relative to the rod.

5. The apparatus of claim 4, wherein the elastically deformable feature is configured to fold the outer portion of stapled tissue relative to the inner portion of stapled tissue.

6. The apparatus of claim 4, wherein the elastically deformable feature is configured to retain the at least one outer portion of stapled tissue in an inwardly folded position relative to the inner portion of stapled tissue within a circular cut line formed by the knife member.

7. The apparatus of claim 1, further comprising:
   (a) an end effector, wherein the end effector comprises:
      (i) an anvil formed by the first jaw, and
      (ii) a lower jaw formed by the second jaw, wherein the anvil is pivotable toward the lower jaw to capture tissue between the anvil and the lower jaw, wherein the staple cartridge is secured to the lower jaw; and
   (b) a stapling mechanism in communication with a shaft assembly and the end effector, wherein the stapling mechanism is configured to staple tissue clamped between the anvil and the lower jaw.

8. The apparatus of claim 1, wherein in the stretched state, the buttress is planar.

9. The apparatus of claim 8, wherein in the stretched state, the buttress is coupled with the deck using at least one of adhesive, clips, or hook and loop fasteners.

10. The apparatus of claim 8, wherein in the stretched state, the buttress is configured to be severed in half by a cutting element that traverses a slot during actuation of the staple cartridge.

11. The apparatus of claim 1, wherein the buttress is removably adhered to deck in the stretched state.

12. An apparatus comprising a staple cartridge configured to fit in a first jaw of a pair of jaws of a surgical stapler, wherein the staple cartridge comprises:
   (i) a plurality of staples;
   (ii) a deck, wherein the deck defines a plurality of openings, wherein each opening of the plurality of openings is associated with a corresponding staple of the plurality of staples, such that each staple is configured to pass through a corresponding opening of the plurality of openings; and (iii) a buttress including an elastically deformable feature, wherein the buttress includes first and second opposing terminal ends disposed along a longitudinal direction of the buttress in a stretched state when the buttress is not contacting tissue and the jaws of the surgical stapler are separated from one another with the staple cartridge secured in the first jaw, wherein the first terminal end is configured to be adjacent a first flap region of tissue and the second terminal end is configured to be adjacent a second flap region of the tissue, and wherein the elastically deformable feature is configured to retain the first and second flap regions of the tissue in an inwardly directed position in a subsequent contracted state when the buttress including the elastically deformable feature is detached from the deck, wherein the buttress is formed from a non-elastic fabric with the elastically deformable feature woven into the non-elastic fabric.

13. The apparatus of claim 12, wherein the first and second flap regions of the tissue define an effective width that is smaller than the diameter of a knife member.

14. An apparatus comprising:
(i) a staple cartridge, wherein the staple cartridge comprises:
 (A) a plurality of staples;
 (B) a deck, wherein the deck defines a plurality of openings, wherein each opening of the plurality of openings is associated with a corresponding staple of the plurality of staples, such that each staple is configured to pass through a corresponding opening of the plurality of openings; and
 (C) a buttress including a non-elastic fabric with elastic members woven into the non-elastic fabric, wherein the buttress is configured to transition from a stretched state to a subsequent contracted state, wherein in the contracted state the buttress including the elastic members is detached from the deck; and
(ii) a circular stapler, wherein the circular stapler comprises:
 (A) an anvil, and
 (B) a stapling head assembly, wherein the stapling head assembly comprises:
  (a) a rod configured to engage the anvil;
  (b) a knife member configured to form a circular cut line in tissue, wherein the circular cut line has a diameter; and
  (c) a staple driver;
 wherein the anvil and stapling head assembly are configured to cooperate to clamp and staple tissue; and
 wherein the buttress is configured to prevent first and second flap regions of the tissue from extending outside the diameter of the knife member by automatically moving each the plurality of staples within the diameter of the knife member after the staples are deployed from the staple cartridge into the tissue.

15. The apparatus of claim 14, wherein the first and second flap regions are configured to be drawn radially inwardly toward the rod under the resilient bias imparted by the elastic members of the buttress.

16. The apparatus of claim 15, wherein the first and second flap regions are positioned within the cylindrical plane defined by the circular cut line, such that the tissue defines an effective width that is smaller than the diameter of the knife member.

17. The apparatus of claim 16, wherein the elastic members are configured to prevent the plurality of staples from impeding operation of the circular stapler by preventing the first and second flap regions from extending outwardly from an anastomosis site.

\* \* \* \* \*